(12) United States Patent
Vardon et al.

(10) Patent No.: US 10,894,760 B2
(45) Date of Patent: Jan. 19, 2021

(54) CATALYSTS, SYSTEMS, AND METHODS FOR THE CONVERSION OF BIOMASS TO CHEMICALS

(71) Applicants: Alliance for Sustainable Energy, LLC, Golden, CO (US); Colorado School of Mines, Golden, CO (US)

(72) Inventors: Derek Richard Vardon, Lakewood, CO (US); Steven Thomas Christensen, Golden, CO (US); Katherine Elaine Hurst, Golden, CO (US); Amy Elizabeth Settle, Littleton, CO (US); Michael Brandon Griffin, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 16/461,476

(22) PCT Filed: Nov. 17, 2017

(86) PCT No.: PCT/US2017/062157
§ 371 (c)(1),
(2) Date: May 16, 2019

(87) PCT Pub. No.: WO2018/094145
PCT Pub. Date: May 24, 2018

(65) Prior Publication Data
US 2019/0345090 A1    Nov. 14, 2019

Related U.S. Application Data

(60) Provisional application No. 62/423,831, filed on Nov. 18, 2016.

(51) Int. Cl.
C07C 51/36    (2006.01)
B01J 21/04    (2006.01)
(Continued)

(52) U.S. Cl.
CPC ............. *C07C 51/36* (2013.01); *B01J 21/04* (2013.01); *B01J 21/063* (2013.01); *B01J 21/08* (2013.01);
(Continued)

(58) Field of Classification Search
CPC ....... C07C 51/36; C07C 29/149; C08G 69/28; B01J 21/04; B01J 21/063; B01J 23/44; B01J 35/1014; B01J 35/1019; C23C 16/04
See application file for complete search history.

(56) References Cited

U.S. PATENT DOCUMENTS

| | | | |
|---|---|---|---|
| 2010/0143608 A1* | 6/2010 | Ruiz | C23C 18/1245 427/576 |
| 2012/0107886 A1* | 5/2012 | Albizati | C12P 7/18 435/146 |

(Continued)

FOREIGN PATENT DOCUMENTS

| | | |
|---|---|---|
| WO | 2012142009 A1 | 10/2012 |
| WO | 2016140641 A1 | 9/2016 |

OTHER PUBLICATIONS

She, X. et al., Selective hydrogenation of trans, trans-muconic acid to adipic acid over a titania-supported rhenium catalyst, 2011, ChemSus Chem, vol. 4, pp. 1071-1073 (Year: 2011).*

(Continued)

*Primary Examiner* — Yate' K Cutliff
(74) *Attorney, Agent, or Firm* — Michael A. McIntyre; Sam J. Barkley

(57) ABSTRACT

The present disclosure relates to a composition that includes a solid support, a metal positioned on the solid support, and an oxide coating positioned to at least partially cover the metal. The compositions described herein may be utilized in methods that include contacting muconic acid and hydrogen
(Continued)

to convert at least a portion of the muconic acid to adipic acid.

14 Claims, 19 Drawing Sheets

(51) Int. Cl.
| | |
|---|---|
| *B01J 21/06* | (2006.01) |
| *B01J 23/44* | (2006.01) |
| *B01J 21/08* | (2006.01) |
| *B01J 35/10* | (2006.01) |
| *B01J 37/02* | (2006.01) |
| *C23C 16/40* | (2006.01) |
| *C23C 16/455* | (2006.01) |
| *C07C 29/149* | (2006.01) |

(52) U.S. Cl.
CPC .......... *B01J 23/44* (2013.01); *B01J 35/1014* (2013.01); *B01J 35/1019* (2013.01); *B01J 37/0225* (2013.01); *C07C 29/149* (2013.01); *C23C 16/40* (2013.01); *C23C 16/403* (2013.01); *C23C 16/45555* (2013.01)

(56) References Cited

U.S. PATENT DOCUMENTS

| | | | |
|---|---|---|---|
| 2013/0232853 | A1 | 9/2013 | Peterson et al. |
| 2014/0094635 | A1* | 4/2014 | Lu .................. C23C 16/45531 585/658 |
| 2014/0096438 | A1 | 4/2014 | Lange |
| 2014/0273118 | A1 | 9/2014 | Held et al. |
| 2015/0099868 | A1 | 4/2015 | Yang et al. |
| 2016/0311746 | A1* | 10/2016 | Pinkos .................. C07C 51/36 |
| 2018/0333774 | A1 | 11/2018 | Christensen et al. |
| 2020/0061598 | A1 | 2/2020 | Vardon et al. |

OTHER PUBLICATIONS

Wang, C., et al., Sub-nanometer-thick Al2O3 overcoat remarkably enhancing thermal stability of supported gold catalyst, Oct. 27, 2016, Chinese Journal of Chemical Physics, vol. 29, No. 5, pp. 571-575 (Year: 2016).*

Yang, N., et al., Investigating the function of metal oxide promoters on syngas conversion to oxygenates through supported Rh catalysts for syngas conversion to oxygenates through surface and interface modification, 2015, Abstract of Papers, 249th ACS National meeting, slides, 15 pages (Year: 2015).*

Draths, K.M., et al., Enviormentally compatible synthesis of adipic acid from D-glucose, 1994, Journal of the American Chemical Society, vol. 116, pp. 399-400 (Year: 1994).*

Lu, J., et al., Coking- and sintering-resistant palladium catalysts achieved through atomic layer deposition, 2012, Science, vol. 335, 1205 pp. 1205-1208 (Year: 2012).*

Lu, J. et al., Coking- and sintering-resistant palladium catalyst achieved through atomic layer deposition, 2012, Science, vol. 335, 1205, on-line supplementary materials, 30 pages (Year: 2012).*

Camacho-Bunquin, J. et al., "Catalyst synthesis and evaluation using an integrated atomic layer deposition synthesis-catalysis testing tool," AIP Review of Scientific Instruments, 2015, vol. 86, pp. 084103-1 through 084103-7.

Dutta, S., "Lignin Deconstruction: Chemical and Biological Approaches," Elsevier Sustainable Catalytic Processes, Chapter 5, 2015, pp. 121 through 155.

Lu, J. et al., "Porous Alumina Protective Coatings on Palladium Nanoparticles by Self-Poisoned Atomic Layer Deposition," ACS Chemistry of Materials, 2012, vol. 24, pp. 2047-2055.

Lu, J. et al., "Atomic layer deposition—Sequential self-limiting surface reactions for advanced catalyst "bottom-up" synthesis," Elsevier Surface Science Reports, 2016, vol. 71, pp. 410-472.

O'Neill, B. et al., "Catalyst Design with Atomic Layer Deposition," ACS Catalysis, 2015, vol. 5, pp. 1804-1825.

Shang, Z. et al., "Encapsulation of supported metal nanoparticles with an ultra-thin porous shell for size-selective reactions," RSC ChemComm Communication, 2013, vol. 49, pp. 10067-10069.

Zhang, H. et al., "Atomic Layer Deposition Overcoating: Tuning Catalyst Selectivity for Biomass Conversion," Wiley, Angewandte Communications, International Edition, 2014, vol. 53, pp. 12132-12136.

Written Opinion from corresponding PCT patent application No. PCT/US17/62157 dated Jan. 12, 2018, 5 pages.

International Search Report from corresponding PCT patent application No. PCT/US17/62157 dated Jan. 12, 2018, 3 pages.

* cited by examiner

CATALYSTS, SYSTEMS, AND METHODS FOR THE CONVERSION OF BIOMASS TO CHEMICALS

CROSS-REFERENCE TO RELATED APPLICATIONS

This application claims the benefit of U.S. Provisional Application No. 62/423,831 filed Nov. 18, 2016 and PCT application PCT/US2017/062157 having an International Filing Date of Nov. 17, 2017, the contents of both of which are incorporated herein by reference in their entirety.

CONTRACTUAL ORIGIN

The United States Government has rights in this disclosure under Contract No. DE-AC36-08GO28308 between the United States Department of Energy and the Alliance for Sustainable Energy, LLC, the Manager and Operator of the National Renewable Energy Laboratory.

BACKGROUND

Adipic acid is a major component of nylon-6,6 and is currently produced from the nitric acid oxidation of cyclohexanone. Adipic acid is produced in excess of 2,600 kta with a price of greater than $1.70 per kg. Due to its industrial importance, significant efforts are underway to produce adipic acid renewably. At the National Renewable Energy Laboratory (NREL), a hybrid biological and chemocatalytic process has been developed to funnel both sugar and lignin-derived monomers into muconic acid as an intermediate for adipic acid production. Muconic acid can be hydrogenated in the condensed phase over platinum group metals, with Pd being the most active. However, Pd is very susceptible to leaching into solution. Platinum group metal (PGM) leaching can prohibit industrial scaling of catalytic processes due to the dramatic negative cost impact. Furthermore, although activated carbon catalyst supports have been shown to reduce leaching, they are highly susceptible to fouling from muconic acid. Thus, there remains a need for improved catalysts, systems, and/or methods for converting biomass to useful fuels and/or chemicals, for example, adipic acid.

SUMMARY

An aspect of the present disclosure is a composition that includes a solid support, a metal positioned on the solid support, and an oxide coating positioned to at least partially cover the metal. In some embodiments of the present disclosure, the oxide may include at least one of silica, titanium oxide, and/or alumina. In some embodiments of the present disclosure, the solid support may have a first characteristic length between 1 micron and 10 mm. In some embodiments of the present disclosure, the metal may include at least one of ruthenium, rhodium, palladium, silver, osmium, iridium, platinum, and/or gold. In some embodiments of the present disclosure, the metal may be present at a concentration between 0.1 wt % and 5.0 wt % relative to the metal and the solid support. In some embodiments of the present disclosure, the metal may be in the form of a particle having a second characteristic length of less than one micron.

In some embodiments of the present disclosure, the oxide coating may include at least one of silica, alumina, titanium oxide, cerium oxide, magnesium oxide, tin oxide, and/or nickel oxide. In some embodiments of the present disclosure, the oxide coating may have a thickness between 0.1 nm and 100 nm. In some embodiments of the present disclosure, the oxide coating may include at least one of a crack or a pore. In some embodiments of the present disclosure, the oxide coating may include between two oxide coatings and five oxide coatings. In some embodiments of the present disclosure, the oxide coating may provide an accessibility to the metal between 80% and 100% as measured by carbon monoxide chemisorption. In some embodiments of the present disclosure, the composition may further include a surface area between 25 $m^2$/g and 200 $m^2$/g as measured by nitrogen physisorption.

In some embodiments of the present disclosure, the composition may further include a surface area between 25 $m^2$/g and 200 $m^2$/g as measured by nitrogen physisorption, where the metal may include palladium, the solid support may include at least one of titanium dioxide and/or alumina, the oxide coating may include between one oxide coating and five oxide coatings of at least one of titanium dioxide or alumina, each oxide coating may have a thickness between 1 nm and 5 nm, the metal may have an accessibility between 85% and 95% as measured by carbon monoxide chemisorption, the metal may be present at a concentration between 0.1 wt % and 1 wt % relative to the metal and the solid support, and the solid support may be in the form of a cylinder having a characteristic length between 0.5 mm and 5 mm.

An aspect of the present disclosure is a method that includes contacting muconic acid and hydrogen with a catalyst that includes a solid support, a metal positioned on the solid support, and an oxide coating positioned to at least partially cover the metal, where the contacting is performed with the muconic acid in a liquid phase comprising an alcohol, and the contacting converts at least a portion of the muconic acid to adipic acid. In some embodiments of the present disclosure, the alcohol may include ethanol. In some embodiments of the present disclosure, the hydrogen may be supplied at a pressure between 1 atmosphere and 100 atmosphere. In some embodiments of the present disclosure, the contacting may be performed in a stirred tank reactor. In some embodiments of the present disclosure, the contacting may be performed at a temperature between 20° C. and 100° C. In some embodiments of the present disclosure, the contacting may be performed in a packed-bed reactor. In some embodiments of the present disclosure, the catalyst may have a characteristic length between about 0.5 mm and 5 mm.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 8A for uncoated $Pd/Al_2O_3$;

FIG. 8B for 1-cycle (1 coating) of $Al_2O_3$ ALD on $Pd/Al_2O_3$; FIG. 8C for 5-cycles (5 coatings) of $Al_2O_3$ ALD on $Pd/Al_2O_3$; and FIG. 8D for 10-cycles (10 coatings) of $Al_2O_3$ ALD on $Pd/Al_2O_3$.

REFERENCE NUMBERS

Figure 1:
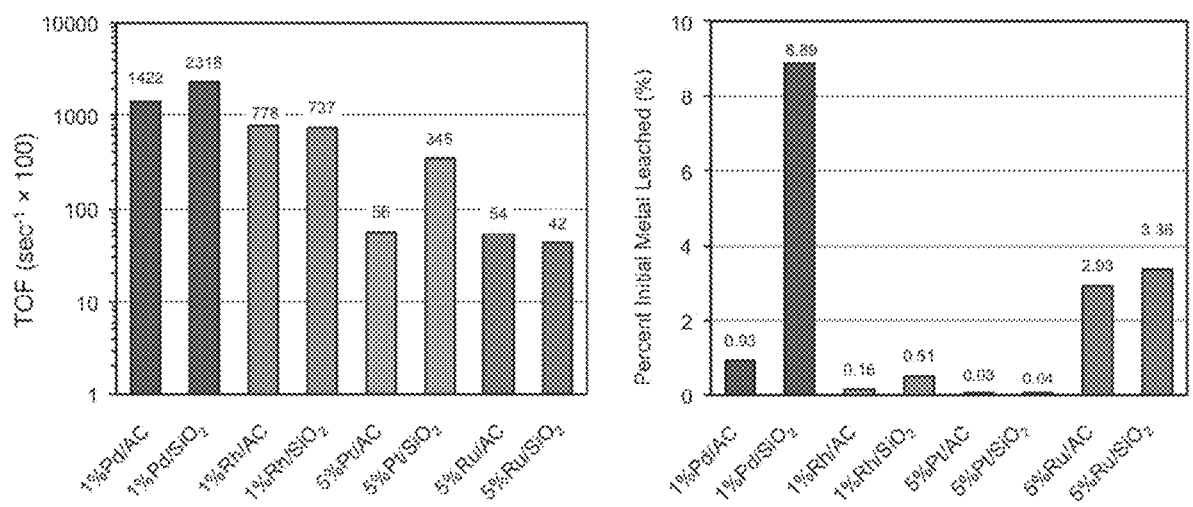
FIG. 1 illustrates muconic acid hydrogenation activity by PGMs on powder activated carbon and silica supports in batch reactions (left panel), and PGM leaching after 35 minutes exposure to reaction conditions (right panel). Reaction conditions were as follows: 20 mL 1 wt % (of solution) muconic acid in ethanol, 24° C., 24 bar $H_2$, 15 mg catalyst, stirring 1600 rpm. Batch reactions were performed in duplicate, with average values reported. Turn over frequencies (TOF) for muconic acid hydrogenation were calculated based on pseudo-first order rate constants fitted for duplicate reactions, by dividing the rate of muconic acid consumption (molar basis) at 10% conversion by the moles of surface-exposed active metal determined by chemisorption. Metal leaching was based on a single leaching measurement from combined solutions of duplicate reactors.

100 . . . catalyst
110 . . . solid support
120 . . . particle
130 . . . coating
200 . . . method
210 . . . contacting
220 . . . muconic acid
230 . . . hydrogen ($H_2$)
240 . . . adipic acid

DETAILED DESCRIPTION

The present disclosure may address one or more of the problems and deficiencies of the prior art discussed above. However, it is contemplated that some embodiments as disclosed herein may prove useful in addressing problems and deficiencies in a number of other technical areas. Therefore, the embodiments described herein should not necessarily be construed as limited to addressing any of the particular problems or deficiencies discussed herein.

Muconic acid can be readily hydrogenated in the condensed phase over platinum group metals (PGMs) at 70° C. and 30 bar, with Pd being the most active. However, as shown in FIG. 1, Pd is very susceptible to leaching into solution. Thus, aspects of the present disclosure relate to atomic layer deposition (ALD) for over-coating, as in the application of one or more coatings onto solid catalyst materials, for example e.g. noble metals, resulting in solid catalysts having improved stability. ALD is a form of chemical vapor deposition wherein layer-by-layer growth occurs by self-limiting chemical reactions at a surface. The term self-limiting refers to the fact that the chemical precursors involved in ALD react only with surface species and not with themselves. Thin oxide films may be deposited by iteratively exposing the surface to a set of precursors to complete an ALD 'cycle'. Thus, in some embodiments of the present disclosure, ALD may stabilize Pd metal sites against leaching, while still allowing for accessibility to active metal sites. In addition, ALD overcoatings may be applied to a wide-range of solid support materials, e.g. oxides, that may be tuned to mitigate organic fouling observed with activated carbon supports.

As such, in some embodiments of the present disclosure, the use of ALD to deposit at least a one-layer coating onto palladium metal, e.g. nanocrystals, loaded at about 1 wt % on a solid support, e.g. $TiO_2$, are described. The resistance of the resultant ALD coated catalysts to leaching of the palladium and to muconic acid organic fouling is compared to a conventional commercial 1% Pd/AC (palladium on an activated carbon support) catalyst. Both classes of catalyst were initially characterized and exposed to muconic acid in ethanol solutions overnight to cause fouling of the catalysts by organic adsorption. Fouled catalysts were then screened to determine their catalytic activity and susceptibility to leaching of the palladium in order to evaluate the benefits of ALD coatings for stabilizing muconic acid hydrogenation catalysts.

Figure 2:
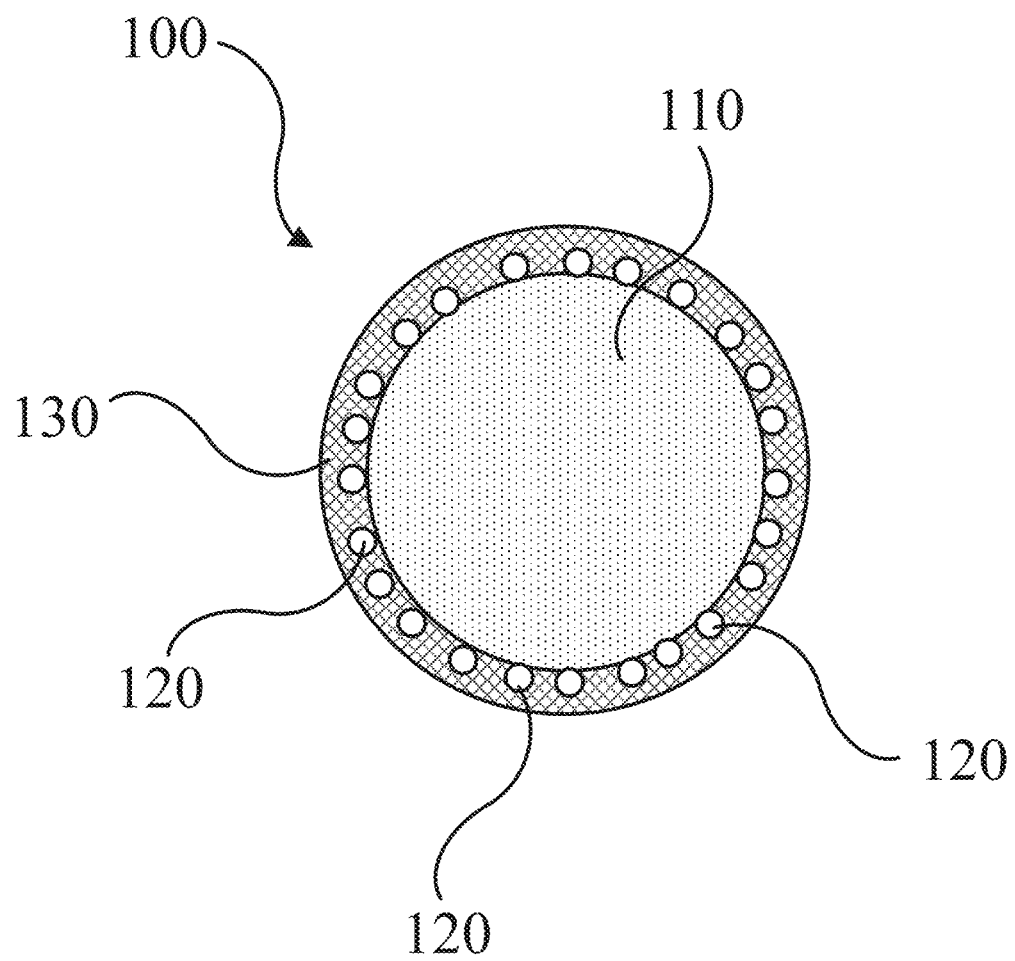
FIG. 2 illustrates a hierarchical composite catalyst having a catalyst solid support with particles, in this case nanoparticles, that are over-coated with a coating, according to some embodiments of the present disclosure. The coating may adopt a porous nature that may enable mass transport to the nanoparticles but may also act to prevent agglomeration of the nanoparticles, dissolution of the nanoparticles, and/or other deleterious effects.

FIG. 2 illustrates a catalyst 100 that includes a solid support 110 with a plurality of particles 120 positioned on at least one surface of the solid support 110, according to some embodiments of the present disclosure. Further, the plurality of particles 120 may be at least partially covered by a coating 130 such that the coating 130 may act as a protective layer, by preventing removal of the particles 120 from the catalyst 100 and/or coalescence of the particles 120 into fewer and/or larger particles (not shown). In some embodiments of the present disclosure, the particles 120 may provide catalytically active sites that promote a desired reaction; e.g. conversion of muconic acid to adipic acid. Thus, in some embodiments of the present disclosure, the particles 120 may include at least one of a transition metal, and/or a noble metal (e.g. at least one of ruthenium, rhodium, palladium, silver, osmium, iridium, platinum, and/or gold.) Additional active metal materials can include bimetallic or trimetallic particles that are alloys, core-shells, or co-located particles, as well as interfaces between a catalyst active metal particle and the support material.

In some embodiments of the present disclosure a solid support 110 may include at least one of a carbonaceous material (e.g. activated carbon) and/or an oxide (e.g. at least one of $TiO_2$, $Al_2O_3$, $SiO_2$, etc.). A solid porous support 110 may be in substantially spherical and/or cylindrical shape and/or any other suitable shape. The solid support 110 may be in a range of sizes including powders (<50 micron), granules (1 mm), pellets (>1 mm), and monoliths. Monolythic catalysts consist of an extradited solid material containing multiple parallel channels that may have cylinder diameters ranging from 10-150 mm, channel sizes ranging from 1-100 $mm^2$, and lengths ranging from 10-1000 mm, which can be coated with catalytically active species. The particles 120 may include any suitable material that provides sufficient activity, selectivity, and/or yield to convert muconic acid and $H_2$ to adipic acid, and/or complete any other reactions of choice. Thus, in some embodiments of the present disclosure, the particles 120 may include at least one noble metal, such as platinum and/or palladium. The particles 120 may be deposited onto a surface of the solid support 110 by any suitable method, e.g. incipient wetness, ion exchange, strong electrostatic adsorption, nanoparticle dispersion, chemical vapor deposition, and ALD. The particles 110 may assume a shape such as spherical, cylindrical, cubic, octahedral, cuboidal/columnar, tetrahedral, and/or any other suitable shape. The particles 110 may be at least one of crystalline, polycrystalline, and/or amorphous. This includes a range of diameters that include extremely disperse particles with a diameter <1 nm, highly disperse particles with a diameter 1-10 nm, moderately dispersed particles with a diameter of 10-20 nm, and minimally dispersed particles with a diameter >20 nm. The final catalyst 100 may be in substantially spherical and/or cylindrical shape and/or any other suitable shape. The final catalyst may be in a range of sizes including powders (<50 micron), granules (1 mm), and pellets (>1 mm), or embedded monoliths.

Figure 3:
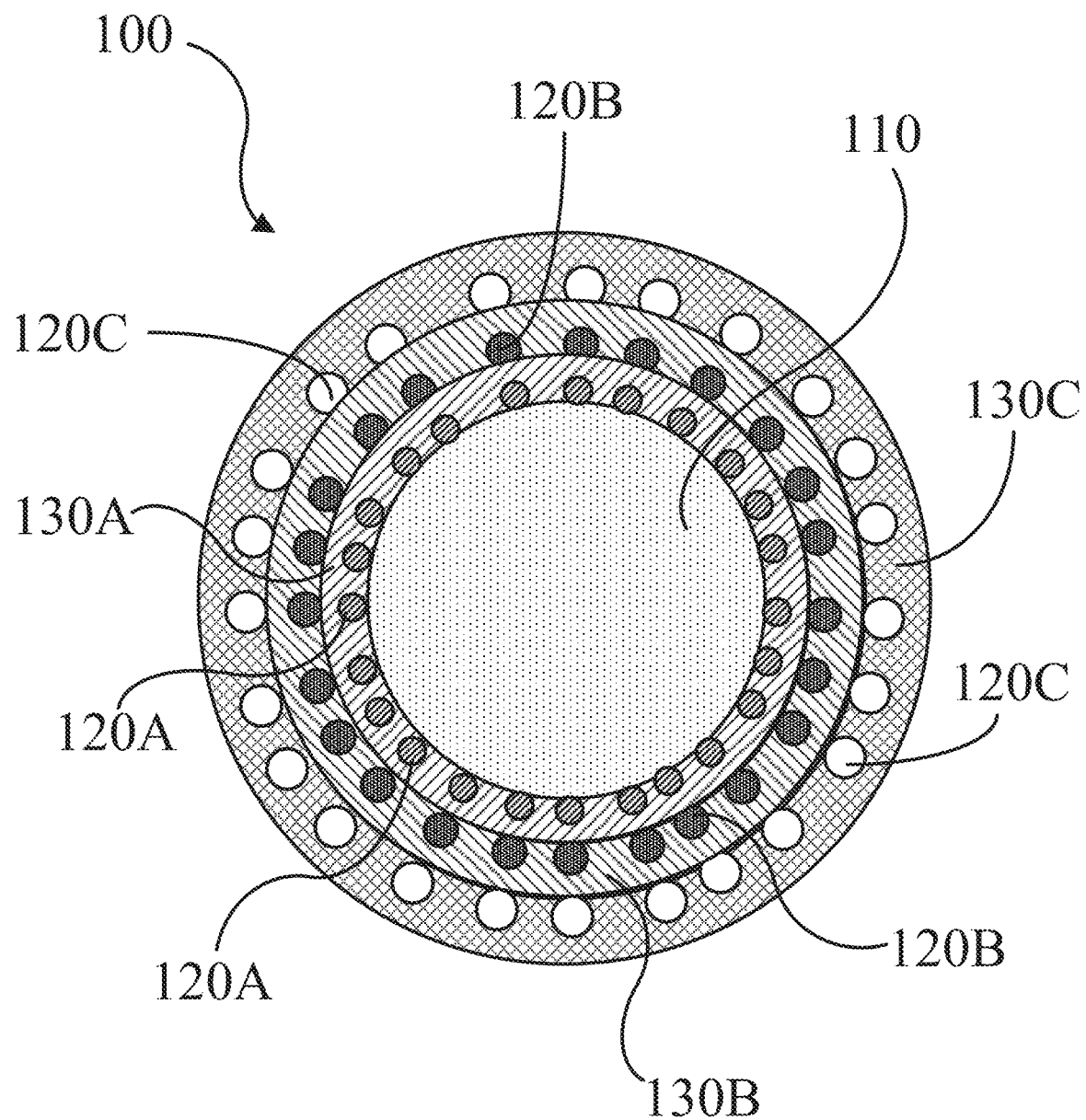
FIG. 3 illustrates a schematic of a catalyst architecture provided by successive depositions that may produce catalysts having multiple compositions and/or hierarchical coatings and/or layers that may serve tailored catalyst purposes, according to some embodiments of the present disclosure.

FIG. 3 illustrates that, in some embodiments of the present disclosure, a catalyst 100 may include more than one particle and/or more than one coating. In addition, a coating (e.g. 130A, 130B, and/or 130B) may be constructed of more than one material, e.g. more than one oxide, by utilizing more than one precursor during the coating formation process (e.g. ALD). For example, FIG. 3 illustrates a catalyst 100 having three layers of distinctly different particles (120A, 120B, and 120C) and coatings (130A, 130B, and 130C). In this case, a first plurality of particles 120A is deposited onto a surface of a solid support 110 and a first coating 130A is deposited such that substantially all of the first particles 120A are covered by the first coating 130A. In addition, a second plurality of particles 120B are deposited onto the first coating 130A and a second coating 130B is deposited such that substantially all of the second particles 120B are covered by the second coating 130B. Finally, a third plurality of particles 120C are deposited onto the second coating 130B and a third coating 130C is deposited such that substantially all of the third particles 120C are covered by the third coating 130C. As used herein, the term "substantially" refers to greater than 98%, greater than 99%, or up to 100%. As described herein, at least one of the coatings (130A, 130B, and/or 130C) may be deposited by ALD. These coatings (130A, 130B, and/or 130C) may include at least one of aluminum oxide ($Al_2O_3$), titanium oxide ($TiO_x$), cerium oxide ($CeO_2$), zirconium oxide ($ZrO_2$), silicon oxide ($SiO_2$), magnesium oxide (MgO), tin oxide ($SnO_2$), and/or nickel oxide (NiO). At least one of the particles (120A, 120B, and/or 120C) may be made of at least one of platinum, palladium, ruthenium, iridium, nickel, and/or rhodium. The coating 130 thicknesses could range from less than one nanometer to five nanometers or more. The coatings (130A, 130B, and/or 130C) may adopt a form of complete layers or partial layers that decorate specific targeted surfaces of the catalyst (e.g. specific crystallographic facets) the catalyst 100, the solid support 110, and/or the particles (120A, 120B, and/or 120C). Beyond improving catalyst stability, additional functionality of at least one of the coatings (130A, 130B, and/or 130C) may include enhanced catalyst chemical activity and/or selectivity. Further, these coatings (130A, 130B, and/or 130C) may be deposited on a variety of solid supports including powders, spheres, granules, pellets, and/or monoliths.

In some embodiments of the present disclosure a coating on a catalyst, as described herein, may have at least one of a crack and/or pore on its surface that may facilitate at least some mass transfer from the catalyst's exterior environment to the particles that are at least partially covered by the coating. Differences in the amount and/or size of cracks and/or pores may be quantified by nitrogen physisorption and carbon monoxide chemisorption as described herein. In some embodiments of the present disclosure, a crack and/or pore may have a characteristic length and/or diameter that is between 30% and 150% of the characteristic length of the particles (e.g. metal particles) of the catalyst. In some embodiments of the present disclosure, the characteristic length of pores or widths of cracks may be smaller than the characteristic length of a particle, if the number of cracks or pores within close proximity to a particle (e.g. metal site) is greater than 2, 3, 4 or 5, where close proximity is defined by a characteristic length scale of at most three times the diameter of a particular metal site adhered to the support. The presence of pores and/or cracks on the catalyst may be observed visually using high resolution imaging techniques.

Figure 4:
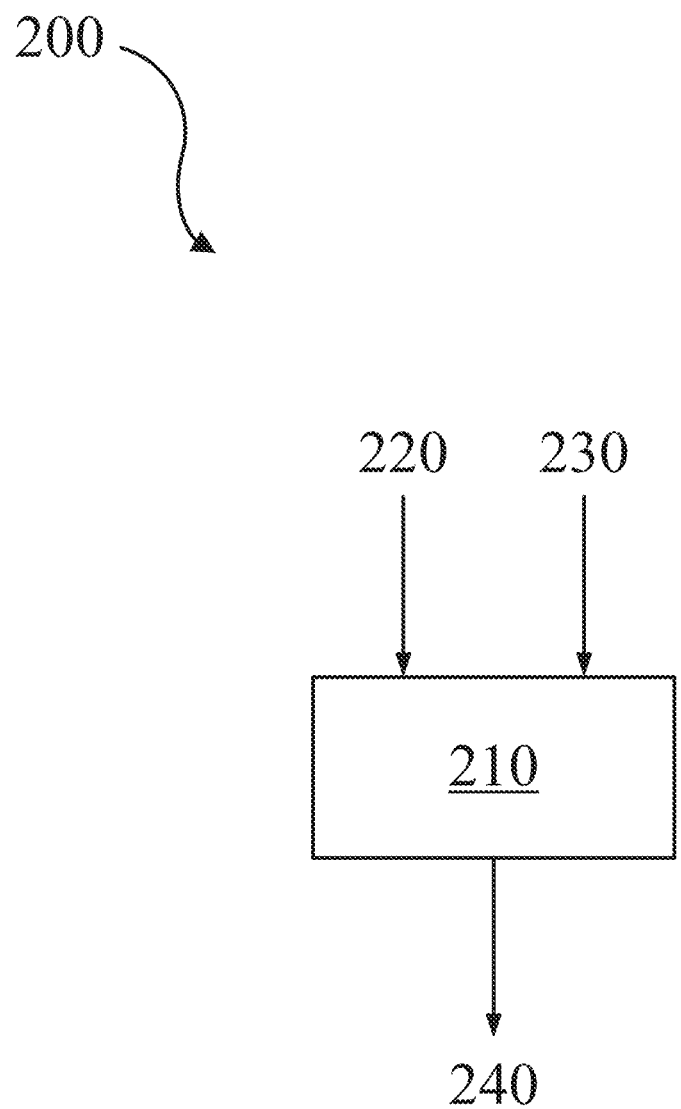
FIG. 4 illustrates a method for converting bio-derived muconic acid and hydrogen to adipic acid using catalysts as described herein, according to some embodiments of the present disclosure.

FIG. 4 illustrates a method 200 for converting muconic acid 220 and hydrogen 230 to adipic acid 240 by contacting 210 the muconic acid 220 and hydrogen 230 with a solid catalyst having features as described above. This method can take place in the condensed phase, vapor phase, or any combination of the two. Reactor configurations may include batch or continuous flow systems such as a three-phase slurry reactor, stirred batch reactor, loop reactor, or packed-bed reactor. Process conditions may range from 20-150° C.

and with a hydrogen pressure from 1-100 bar. For the slurry reactor operation, this includes the use of fine catalyst particles (<100 micron) or granular catalyst particles (100 micron to 1 mm), with muconic acid dissolved in a solvent (e.g., methanol, ethanol, tetrahydrofuran, acetone, acetic acid, ethyl acetate, γ-valerolactone, and/or other solvents in which muconic acid is soluble) from 1-50 wt % in solution, and the catalyst loaded into solution at 1-20 wt % of solution. The slurry reactor can operate with a residence time range from 5 min to 300 min. For the packed bed reactor operation, this includes the use of fine catalyst particles (<100 micron), granular catalyst particles (100 micron to 1 mm), or pellet catalyst particles (>1 mm) with muconic acid dissolved in solvent (e.g., methanol, ethanol, tetrahydrofuran, acetone, acetic acid, ethyl acetate, γ-valerolactone, and/or other solvents in which muconic acid is soluble). The muconic acid solution is fed to the reactor along with hydrogen gas flowing at a hydrogen to muconic acid molar ratio ranging 1:1 to 1:100. The packed bed reactor can operate with a weight hour space velocity (mass of muconic acid processed per mass of catalyst per hour) ranging from 0.05 to 15

Catalyst Materials.

ALD experiments were conducted with a 1% Pd/$SiO_2$ catalyst (e.g. palladium particles deposited on a $SiO_2$ solid support) prepared in-house. A catalyst made of 1% Pd/$SiO_2$ was synthesized as described previously (Green Chem. 18, 3397 (2016)). Blank Davisil Grade 633 high surface area silica was obtained from Sigma Aldrich. This solid support was initially sieved >270 mesh (<53 micron) and calcined at 500° C. in air prior to loading with palladium. Palladium acetate (Sigma Aldrich) was used as the metal precursor and loaded by incipient wetness. After loading, the resultant catalyst, hereinafter referred to as "1% Pd/$SiO_2$ Sigma Aldrich," was dried at 110° C. and reduced in hydrogen flowing at 200 standard cubic centimeters per minute (sccm) for 2 hours at 125° C. The catalyst was then coated by ALD with $Al_2O_3$ using the methodology described below.

In some embodiments, ALD tests were performed with a 1% Pd/$TiO_2$ catalyst (e.g. palladium particles deposited on a $TiO_2$ solid support) prepared in-house. Blank pellet $TiO_2$ support was obtained from Saint-Gobain. The support was ground and sieved to >270 mesh (<53 micron) prior to loading with palladium. Palladium was loaded onto the support by strong electrostatic adsorption. Initially, about 1.98 g of the solid support was added to a beaker with ~60 mL of deionized water. Due to the acidic surface charge of the solid support, the pH of the solution was raised to 11.5-12.0 using NaOH to deprotonate the solid support. In a separate beaker, the target metal cationic precursor, tetraaminepalladium (II) chloride monohydrate, was added to ~30 mL of DI water. Both solutions were then combined and allowed to stir at 350 rpm for at least 2 hours. After stirring, the catalyst particles were vacuum filtered, dried, and reduced in 200 sccm of pure $H_2$ for about 4 hours at 150° C. The Pd-loaded catalyst hereinafter is referred to as "1% Pd/$TiO_2$ Saint-Gobain." The catalyst was then coated by ALD with $Al_2O_3$ using the methodology described below.

In some embodiments, ALD tests were performed with a 1% Pd/$Al_2O_3$ catalyst (e.g. palladium particles deposited on $Al_2O_3$ solid support) obtained commercially in powder form (>50 mesh; <300 μm) from Sigma Aldrich, hereinafter referred to as "1% Pd/$Al_2O_3$ Sigma Aldrich". The catalyst was then coated by ALD with $Al_2O_3$, as received, and separately coated by ALD with $TiO_2$, as received, using the methodology described below.

In some embodiments, ALD tests were performed with a 0.7% Pd/$TiO_2$ catalyst (e.g. palladium particles deposited on a $TiO_2$ solid support) prepared in-house. Blank pellet $TiO_2$ support was obtained Alfa Aesar. The support was ground and sieved to 30-50 mesh (300-600 micron) prior to loading with palladium. Palladium was loaded by strong electrostatic adsorption using pH adjustment with tetraaminepalladium (II) chloride monohydrate. The catalyst was reduced at 150° C. under 200 sccm flowing hydrogen for 4 hours. The Pd-loaded catalyst is hereinafter referred to as "0.7% Pd/$TiO_2$ Alfa Aesar." The catalyst was then coated by ALD with $Al_2O_3$ using the methodology described below.

In some embodiments, ALD tests were performed with an eggshell 0.5% Pd/$Al_2O_3$ catalyst (e.g. palladium particles deposited on an $Al_2O_3$ solid support) obtained commercially in 3.18-mm pellet form from Alfa Aesar, hereinafter referred to as "eggshell 0.5% Pd/$Al_2O_3$ pellets". The catalyst was then coated by ALD with $Al_2O_3$, as received, using the methodology described below. For batch reactor testing, the uncoated and ALD coated eggshell 0.5% Pd/$Al_2O_3$ pellet catalyst was ground and sieved to (>50 mesh; <300 micron) prior to use.

Atomic Layer Deposition.

Oxide-supported palladium catalysts were ALD overcoated using a custom-designed high surface area rotary ALD system. This ALD system is a viscous flow, hot-wall reactor outfitted with four mass flow controllers. The system contained a rotary drive shaft sample holder that enabled physical agitation of granular materials in a tumbler with porous walls to allow precursor diffusion. The rotary ALD system was also equipped with four liquid sources, three heated sources, oxygen, nitrogen and hydrogen. The catalysts were coated by ALD as described below:

1. $Al_2O_3$ coatings were deposited by ALD on the 1% Pd/$SiO_2$ Sigma Aldrich catalyst. The stop flow ALD was performed in the rotary system operated at 125° C. In stop-flow mode, the reactor is isolated from the pump during the exposure to the precursor. The pump is opened either after the exposure of the precursor, or after a defined exposure time. The precursors were trimethylaluminum (TMA) and water, both of which were held in vessels at room temperature. Three samples of ~100 mg of 1% Pd/$SiO_2$ Sigma Aldrich catalyst were coated with 1, 5, and 15 cycles (corresponding to 1, 5, and 15 $Al_2O_3$ layers) of TMA/$H_2O$ to deposit aluminum oxide onto the 1% Pd/$SiO_2$. The timing sequences and carrier gas (99.9999% nitrogen) flows are summarized below in Table 1. Dose is defined as the time that the precursor is introduced into the reactor. Exposure is defined as the time in which the precursor dwells inside the reactor after the dose. Purge if defined as the time to remove the precursor from the reactor via flowing carrier gas. Evacuate is defined as the time to remove the precursor from the reactor with vacuum and no flowing carrier gas.

TABLE 1

| | TMA | | | | $H_2O$ | | | |
|---|---|---|---|---|---|---|---|---|
| | Dose | Exposure | Purge | Evacuate | Dose | Exposure | Purge | Evacuate |
| Time (s) | 60 | 300 | 300 | 0 | 60 | 300 | 300 | 0 |
| MFC 1 (sccm) | 60 | 60 | 60 | 60 | 60 | 60 | 60 | 60 |
| MFC 2 | 20 | 20 | 20 | 20 | 20 | 20 | 20 | 20 |
| MFC 3 | 20 | 20 | 20 | 20 | 20 | 20 | 20 | 20 |
| MFC 4 | 20 | 20 | 20 | 20 | 20 | 20 | 20 | 20 |

2. $Al_2O_3$ coatings were deposited by ALD on the 1% $Pd/TiO_2$ Saint-Gobain catalyst. The 1% $Pd/TiO_2$ Saint-Gobain catalyst was coated by ALD with 5 cycles of $Al_2O_3$ using TMA and $H_2O$ under conditions identical to those in Table 1.

3. $TiO_2$ coatings were deposited by ALD on the 1% $Pd/TiO_2$ Saint-Gobain catalyst. $TiO_2$ was deposited on the catalysts at 295° C. using titanium isopropoxide (TTIP) and water. The TTIP was held at 75° C. and water at room temperature. Three samples of 1, 5, 15 cycles were prepared, corresponding to 1, 5, and 15 layers of $TiO_2$ on the 1% $Pd/TiO_2$ catalysts. Table 2 summarizes the timing and nitrogen carrier gas flows.

TABLE 2

| | TTIP | | | | $H_2O$ | | | |
|---|---|---|---|---|---|---|---|---|
| | Dose | Exposure | Purge | Evacuate | Dose | Exposure | Purge | Evacuate |
| Time (s) | 15 | 180 | 180 | 0 | 15 | 180 | 180 | 0 |
| MFC 1 (sccm) | 20 | 5 | 20 | 20 | 60 | 5 | 20 | 20 |
| MFC 2 | 20 | 5 | 20 | 20 | 20 | 5 | 20 | 20 |
| MFC 3 | 20 | 5 | 20 | 20 | 20 | 5 | 20 | 20 |
| MFC 4 | 60 | 5 | 20 | 20 | 20 | 5 | 20 | 20 |

4. $Al_2O_3$ coatings were deposited by ALD on the 1% $Pd/Al_2O_3$ Sigma-Aldrich catalyst using an ALD fixed bed configuration. The catalyst was held in in a 1.5"×2" stainless steel tray placed horizontally in the reactor without sample agitation. The $Al_2O_3$ precursors, TMA and $H_2O$, were held at room temperature. The 1% $Pd/Al_2O_3$ Sigma Aldrich catalyst was coated by ALD with 1, 5, and 10 cycles of $Al_2O_3$ using stop-flow mode ALD at 200° C. with TMA and $H_2O$ precursors, resulting in 1, 5, and 10 layers of $Al_2O_3$ coatings deposited on the 1% $Pd/Al_2O_3$ catalysts. In stop-flow mode, one half cycle consists of dosing the sample with the precursor, exposure of the sample with the precursor isolated from the pump, a purge at higher flow rates, followed by evacuation of the chamber. These steps were followed for both TMA and $H_2O$. One full cycle consists of two half cycles, the first with TMA and the second with $H_2O$. The timing and carrier gas (99.9999% nitrogen) flow parameters for $Al_2O_3$ ALD are provided below in Table 3.

TABLE 3

| | TMA | | | | $H_2O$ | | | |
|---|---|---|---|---|---|---|---|---|
| | Dose | Exposure | Purge | Evacuate | Dose | Exposure | Purge | Evacuate |
| Time (s) | 3 | 80 | 60 | 15 | 3 | 80 | 60 | 15 |
| MFC 1 (sccm) | 40 | 5 | 40 | 0 | 60 | 60 | 60 | 0 |
| MFC 2 | 60 | 5 | 60 | 0 | 20 | 5 | 60 | 0 |
| MFC 3 | 60 | 5 | 60 | 0 | 20 | 5 | 40 | 0 |
| MFC 4 | 40 | 5 | 40 | 0 | 40 | 5 | 40 | 0 |

5. $TiO_2$ coatings were deposited by ALD on the 1% $Pd/Al_2O_3$ Sigma Aldrich catalyst. The 1% $Pd/Al_2O_3$ Sigma Aldrich catalyst was coated by ALD with $TiO_2$ at 175° C. using the precursors TITIP and $H_2O$. The catalyst was held in in a 1.5"×2" stainless steel tray placed horizontally in the reactor without sample agitation. TITIP was held at 80° C. and $H_2O$ at room temperature. The process was operated in continuous-flow mode where there is no 'exposure' step. In continuous-flow mode, the carrier gas flow is constant and evacuation times are zero. The 1% $Pd/Al_2O_3$ Sigma Aldrich catalyst was coated by ALD with 5 cycles of $TiO_2$ using TITIP and $H_2O$ in continuous-flow mode. Timing and carrier gas (99.9999% nitrogen) flow parameters for $TiO_2$ ALD are provided in Table 4.

TABLE 4

| | TTIP | | | | $H_2O$ | | | |
|---|---|---|---|---|---|---|---|---|
| | Dose | Exposure | Purge | Evacuate | Dose | Exposure | Purge | Evacuate |
| Time (s) | 100 | 0 | 300 | 0 | 100 | 0 | 600 | 0 |
| MFC 1 (sccm) | 40 | 40 | 40 | 40 | 40 | 40 | 40 | 40 |
| MFC 2 | 60 | 60 | 60 | 60 | 60 | 60 | 60 | 60 |
| MFC 3 | 20 | 20 | 20 | 20 | 20 | 20 | 20 | 20 |
| MFC 4 | 40 | 40 | 40 | 40 | 40 | 40 | 40 | 40 |

6. $Al_2O_3$ coatings were deposited by ALD on the 0.7% $Pd/TiO_2$ Alfa Aesar catalyst. The 0.7% $Pd/TiO_2$ Alfa Aesar catalyst was coated by ALD with 5 cycles of $Al_2O_3$ using TMA and $H_2O$ under conditions identical to those in Table 3.

7. $Al_2O_3$ coatings were deposited by ALD on the eggshell 0.5% $Pd/Al_2O_3$ pellet catalyst. The eggshell 0.5% $Pd/Al_2O_3$ pellet catalyst was coated by ALD with 15 cycles of $Al_2O_3$ using TMA and $H_2O$ under conditions identical to those in Table 3.

Catalyst Characterization:

The catalysts described above were characterized by various methods as described below.

Nitrogen Physisorption.

Nitrogen physisorption was performed to measure the surface area of catalyst samples. The BET surface area and pore volume of the prepared catalysts were measured with an ASAP 2020 using a 55-point nitrogen adsorption/desorption curve at −196° C. Prior to analysis, the sample was degassed at 300° C. for five hours under vacuum. BET surface areas were determined over a relative pressure range of 0.060 to 0.200 $P/P_0$. Pore size distributions were calculated using the BJH method off of the adsorption branch of the isotherms over a relative pressure range of 0.140 to 0.995 $P/P_0$.

Elemental Analysis.

Inductively coupled plasma mass spectrometry (ICP-MS) was used to measure catalyst elemental composition and amount of leached Pd after batch and flow reactions. Initially, the amount of Pd leaching after batch reactor tests for the uncoated 1% $Pd/SiO_2$ Sigma Aldrich, $Al_2O_3$ ALD coated 1% $Pd/SiO_2$ Sigma Aldrich, 1% Pd/AC, and $Al_2O_3$ ALD coated 1% $Pd/TiO_2$ Saint-Gobain catalysts was measured after filtering out the catalyst and analyzing the combined ethanol and organic acid solution. For these catalyst materials, Pd leaching is reported as the percent (mass basis) of Pd leached into solution per Pd initially loaded into the batch reactor as part of the catalyst. To improve the detection limit for Pd leaching with subsequent catalyst materials, (i.e., 1% $Pd/Al_2O_3$ Sigma-Aldrich, 0.7% $Pd/TiO_2$ Alfa Aesar, eggshell 0.5% $Pd/Al_2O_3$ pellet, including catalyst samples with and without ALD coatings), the ethanol solution was evaporated and dried to concentrate leached Pd into the solid organic acid fraction prior to ICP analysis. For these catalyst materials, Pd leaching is reported as the parts per million (mass basis) of Pd leached into the solid organic acid fraction processed in the batch or flow reactor.

Chemisorption.

Chemisorption was conducted to measure the amount of accessible surface Pd sites on catalyst samples. $H_2$ chemisorption measurements were conducted using a Micromeritics Autochem II 2920 pulse analyzer. Prior to $H_2$ chemisorption analysis, catalysts samples (~50-100 mg) were degassed at 40° C. for 0.2 hours under Ar, dried at 100° C., reduced at 280° C. in flowing 10% $H_2$/Ar (50 mL min$^{-1}$) for 1 hour, and purged at 280° C. for 0.5 hours with Ar. When calculating turn over frequency, a Pd:H stoichiometry of one-to-one was assumed. CO chemisorption measurements were conducted using an Altamira AMI-390 microflow reactor system equipped with a thermal conductivity detector (TCD). Samples of ~50-100 mg were loaded in a quartz U-tube reactor and heated in 5% $H_2$/Ar to 140° C. at 5° C. min$^{-1}$ with a hold time of 2 hours. After the reduction step, catalyst samples were flushed with helium at 50 mL min$^{-1}$ for 1 hour to remove any weakly adsorbed hydrogen. The samples were then cooled to 30° C. and dosed with sequential 500 microliter pulses of 10% CO/He mixture. A 500-microliter sample loop was used to calibrate the TCD response for CO after each experiment. When calculating turn over frequency, a Pd:CO stoichiometry of one-to-one was assumed.

SEM-EDS.

Scanning electron microscopy energy dispersive x-ray spectroscopy (SEM-EDS) was used to collect images and elemental maps of catalyst samples. SEM-EDS was performed on a FEI Quanta 400 FEG SEM under high vacuum equipped with an Everhart Thorney detector and an EDAX x-ray detector. Samples were mounted on aluminum stubs using conductive carbon tape to reduce sample charging. Imaging and mapping was performed using accelerating voltages from 12.5 to 20 kV.

Catalyst Testing:

The catalysts described above were tested by various methods as described below.

Catalyst Fouling Susceptibility.

To evaluate the resistance to organic fouling by adsorption, catalysts were exposed to ethanol solutions of muconic acid. Initially, 100 mg of catalyst was added to 30 g of a fully dissolved solution containing 1 wt % muconic acid in ethanol. The solutions were then stirred overnight and filtered through a 0.2-micron filter and rinsed with 20 mL of ethanol. Filtrates were analyzed by ICP to determine the extent of initial metal leaching. The filtered and rinsed catalysts were then dried overnight at 110° C. in air using an oven, prior to hydrogenation testing.

Muconic Acid Hydrogenation.

The activity of fresh and fouled catalysts was measured in a Parr multi-batch reactor system in duplicate. For each test, 15 mg of catalyst was added to 20 g of solution containing 2 wt % muconic acid in ethanol. The reactor was stirred at 1600 rpm and pressurized to 24 bar of $H_2$. Periodic samples were collected using a syringe through a custom reactor head sampling port. The samples were then filtered and analyzed by high-performance liquid chromatography (HPLC) to determine the extent of muconic acid conversion. After the reaction was complete, the reactor contents were vacuum filtered (0.2-micron PES filter assembly, Nalgene) to remove catalyst particles, and subsequently the liquid filtrate was analyzed by ICP to examine the extent of palladium leaching from each catalyst.

Batch Reactor Testing.

Batch reactor testing was performed to measure changes in catalyst activity and leaching stability before and after ALD coating of the catalysts by the methods described above. The reduction of muconic acid was modeled as pseudo-first order to estimate the rate constant. Batch reactor catalyst hydrogenation productivity was calculated by dividing the rate of muconic acid consumption (mass basis) at 10% conversion by the total mass of catalyst loaded into the reactor. Catalyst TOF was calculated by dividing the rate of muconic acid consumption (molar basis) at 10% conversion by the moles of surface-exposed Pd determined by chemisorption.

Continuous Flow Reactor Testing.

Continuous flow reactor testing was conducted with down-selected catalysts to measure changes in prolonged activity (>24 hours) and leaching stability before and after ALD coating of the catalysts by the methods described above. Testing was performed using a Parr tubular reactor system (Parr Instruments) operated in a down-flow trickle-bed configuration. The reactor system was outfitted with a HPLC pump (Series III Scientific Instrument) to deliver liquid phase reactants, two mass flow controllers (Brooks Instrument) to control inert gas and $H_2$ gas delivery, tube-in-tube heat exchanger for cooling the reactor effluent, high-pressure 1-L stainless steel knockout pot with bottom sampling valve, and a solenoid-controlled backpressure regulator (Tescom) to maintain system pressure. Reactions were performed with gas and liquid reagents fed to through the top of a 32" long, ¼" inner-diameter stainless steel reaction tube surrounded by a clamshell furnace. The tube temperature was monitored and controlled using an internal thermocouple centered in the catalyst bed and three furnace wall thermocouples. The tube was initially packed halfway with inert 1-mm glass beads (Sigma Aldrich) held in place with quartz wool (Quartz Scientific Inc.). The catalyst bed was then loaded at the tube mid-height. Inert quartz sand (Quartz Scientific Inc.) sieved to fit through a 60-mesh opening (250 micron) and placed at the base and top of the catalyst packing to serve as a support. The remaining reactor tube void was then filled with inert glass beads and sealed with quartz wool. Continuous hydrogenation reactions were performed with $H_2$ supplied at 200 sccm and a system pressure maintained at 500 psig. The mobile phase consisted of commercial cis,cis-muconic acid (Sigma Aldrich) dissolved in 200-proof ethanol (muconic acid 8 g L$^{-1}$). Commercial succinic acid (Sigma Aldrich) was added as an internal standard (succinic acid 0.8 g L$^{-1}$). The mobile phase was delivered at a flow rate of 0.5 mL min$^{-1}$. Liquid effluent samples were collected from the knockout pot, syringe-filtered, and analyzed by HPLC. Subsamples of the liquid filtrate were also filtered and the solvent was removed by blow-down to quantify leached Pd by ICP-MS. Flow reactor runs were conducted for at least 24 hours. Flow reactor catalyst hydrogenation productivity was calculated by dividing mass of muconic acid converted per hour per mass of catalyst loaded into the reactor.

Figure 5:
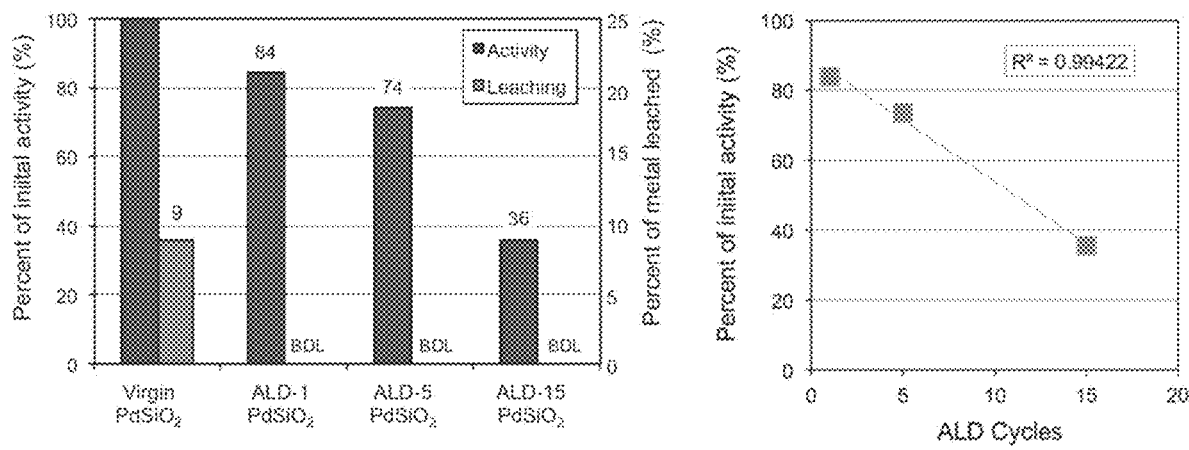
FIG. 5 illustrates activity and leaching susceptibility for the fresh uncoated catalyst and atomic layer deposition (ALD) $Al_2O_3$ overcoated 1 wt % $Pd/SiO_2$ catalyst prepared in-house using a Sigma Aldrich $SiO_2$ support, produced according to some embodiments of the present disclosure. Metal leaching was based on a single leaching measurement from combined solutions of duplicate reactors. Reaction conditions were as follows: 20 mL 1 wt % muconic acid in ethanol, 24° C., 24 bar $H_2$, 15 mg catalyst, stirring 1600 rpm.

Results:

ALD oxide coatings mitigated palladium leaching during the hydrogenation of muconic acid. To provide a proof-of-concept demonstration for the use of ALD to mitigate palladium leaching with muconic acid hydrogenation, an initial suite of 1% Pd/SiO$_2$ catalysts with varying cycles of Al$_2$O$_3$ ALD, resulting in corresponding numbers of Al$_2$O$_3$ ALD layers on the catalysts, were synthesized and screened (see FIG. 5). For the non-ALD coated catalyst using a SiO$_2$ solid support, the leaching of palladium was extensive with over 9% of the initial palladium loaded on the catalyst leaching from the catalyst into solution. However, a palladium on SiO$_2$ catalyst having a single layer of Al$_2$O$_3$ deposited by ALD onto the palladium particles demonstrated no detectable leaching of the palladium into solution by ICP. Catalysts with additional cycles of ALD (and, as a result, additional Al$_2$O$_3$ layers) further reduced the activity of the catalyst, with no detectable leaching of palladium into solution by ICP. As described below, further ALD catalyst development was conducted with a low surface area $TiO_2$ support.

Figure 6:
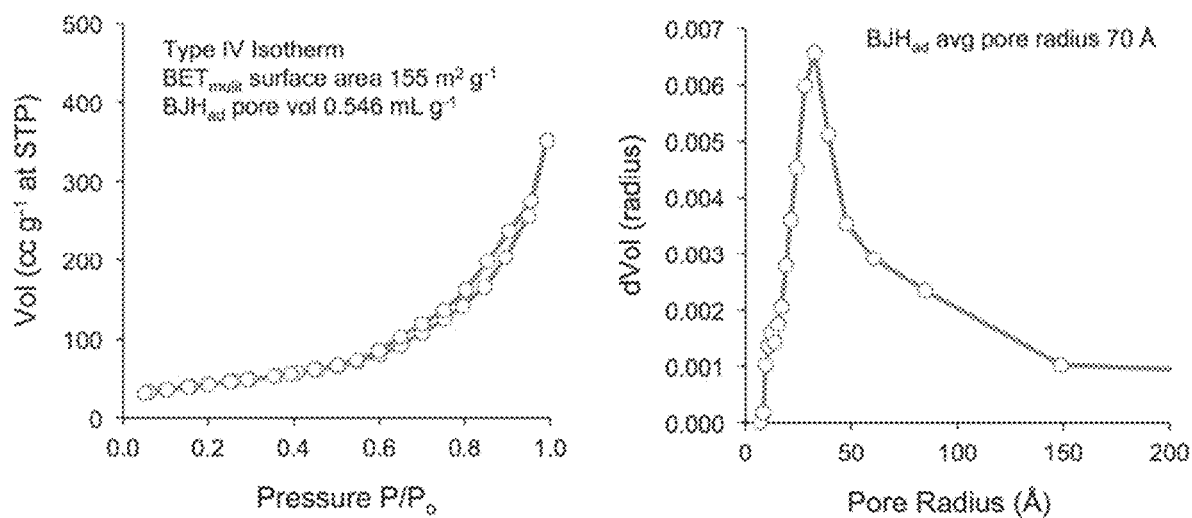
FIG. 6 illustrates for the $TiO_2$ catalyst support obtained from Saint-Gobain, a nitrogen physisorption isotherm profile, surface area, average pore volume (left), pore radius distribution, and average pore radius (right), according to some embodiments of the present disclosure.

Using a low surface area oxide catalyst support (<250 m$^2$ g$^{-1}$) may reduce organic fouling during muconic acid hydrogenation and may result in improved sustained catalytic activity. To evaluate the impact of the catalyst support selection on the ability to resist fouling, a commercial 1% Pd/AC (e.g. palladium on an activated carbon solid support) catalyst was compared to a 5-cycle ALD $Al_2O_3$ coated 1% Pd/$TiO_2$ catalyst. Previous characterization of the commercial 1% Pd/AC catalyst confirmed its high surface area (825 m$^2$ g$^{-1}$), and AC is a known adsorbent for muconic acid which can lead to fouling of exposed metal sites. In contrast, the $TiO_2$ support showed a much lower surface area (155 m$^2$ g$^{-1}$), broad pore size distribution, and a high average pore radius of 70 Å (see FIG. 6).

Figure 7:
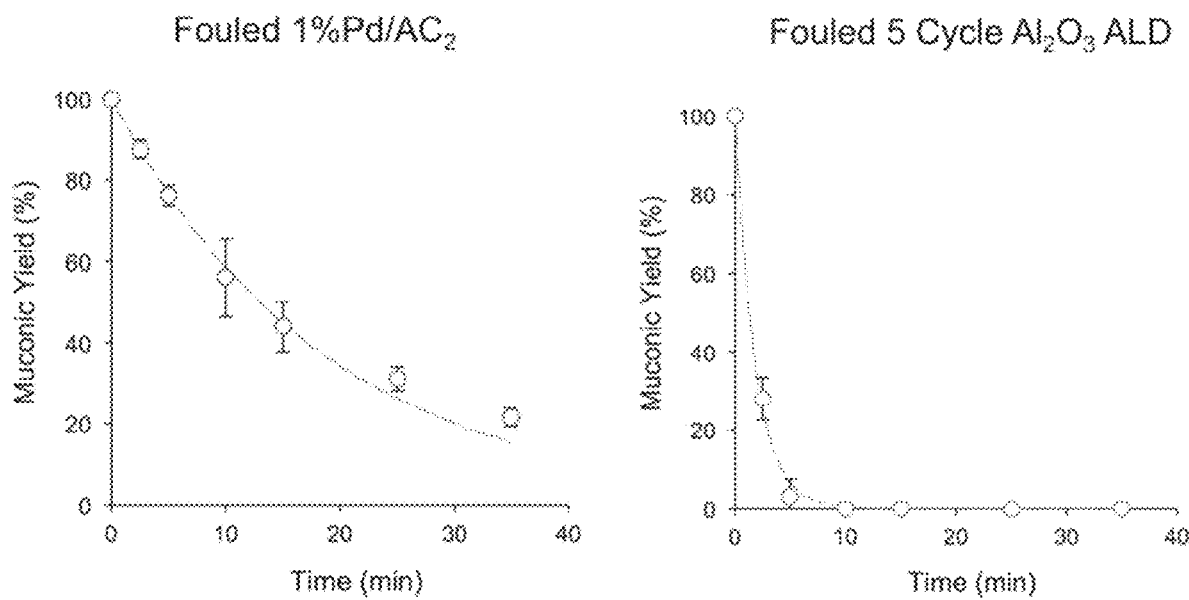
FIG. 7 illustrates fouled catalyst activity for muconic acid hydrogenation with a commercial 1 wt % Pd on activated carbon (AC) catalyst from Alfa-Aesar (left) and 5-cycle $Al_2O_3$ ALD coated 1 wt % $Pd/TiO_2$ catalyst prepared in-house using a Saint-Gobain $TiO_2$ support (right), according to some embodiments of the present disclosure.
Figure 8A:
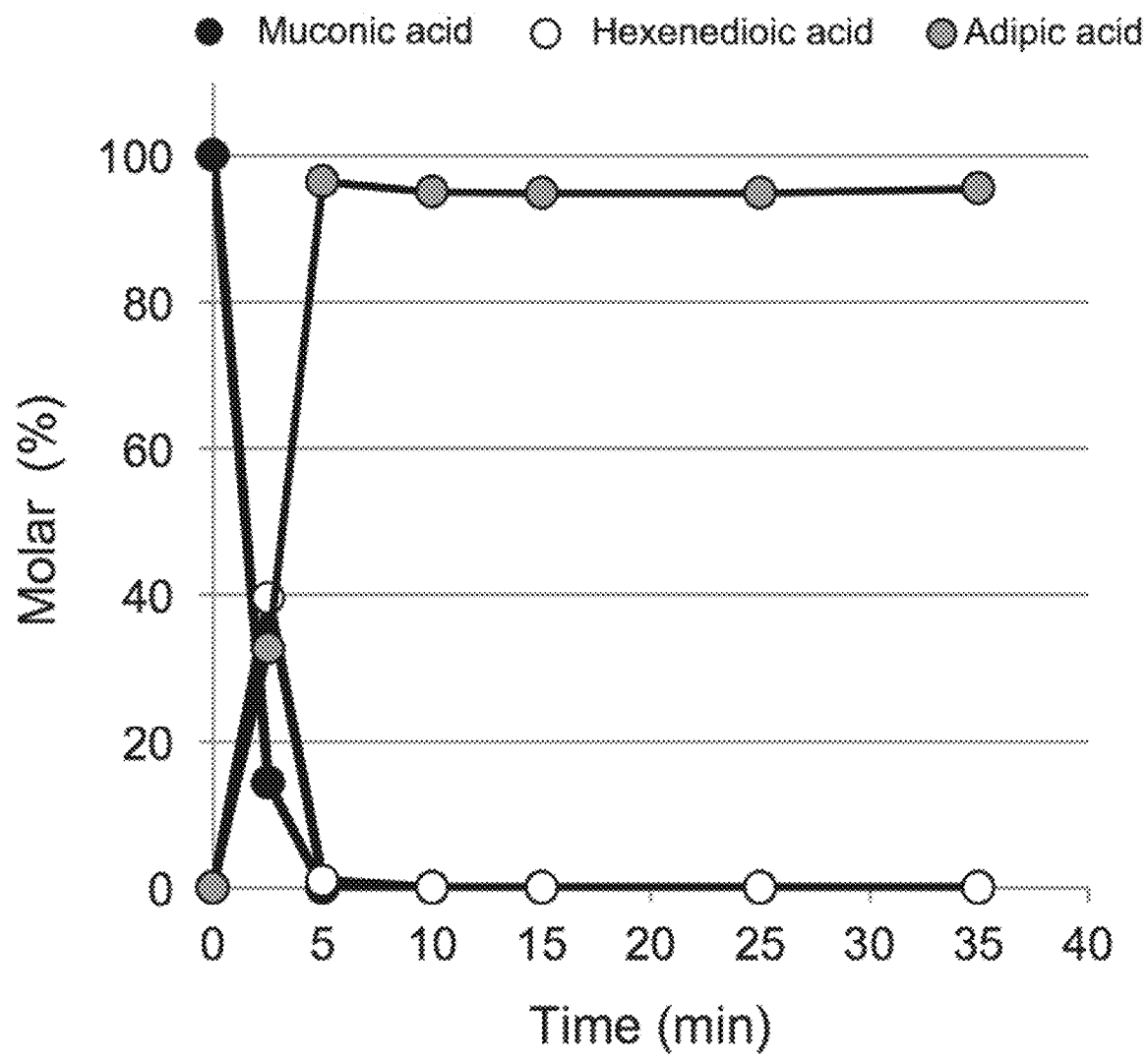
FIGS. 8A-8D illustrate catalyst activity and selectivity of the uncoated and $Al_2O_3$ ALD coated 1% $Pd/Al_2O_3$ Sigma Aldrich catalyst suite ranging from 1 to 10 ALD cycles, according to some embodiments of the present disclosure. Reaction conditions were as follows: 20 mL 1 wt % muconic acid in ethanol, 24° C., 24 bar $H_2$, 15 mg catalyst, stirring 1600 rpm. Pd leaching was measured after the reaction by filtering out the catalyst and measuring the Pd content of the organic acid product mixture by ICP-MS.
Figure 8B:
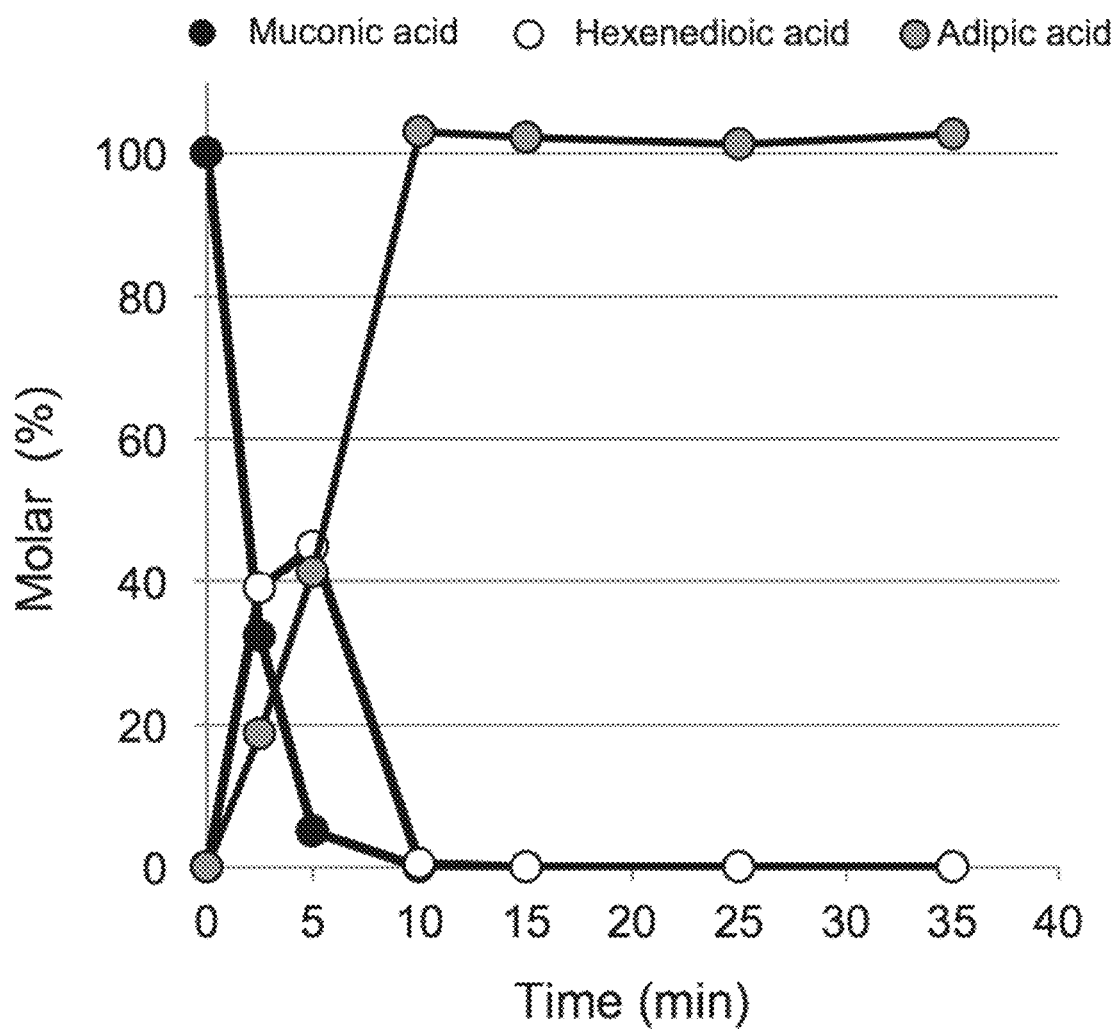
Figure 8C:
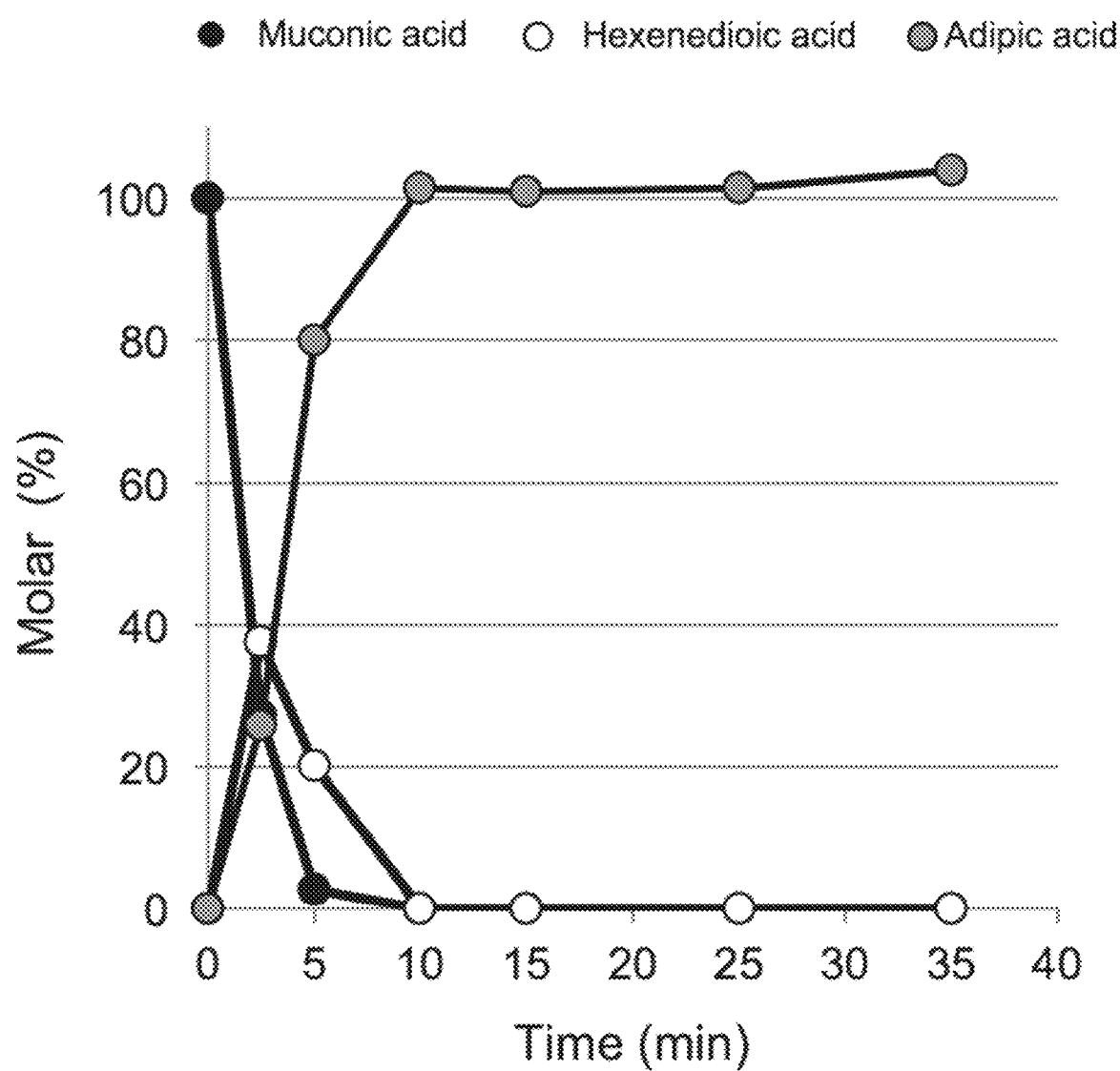
Figure 8D:
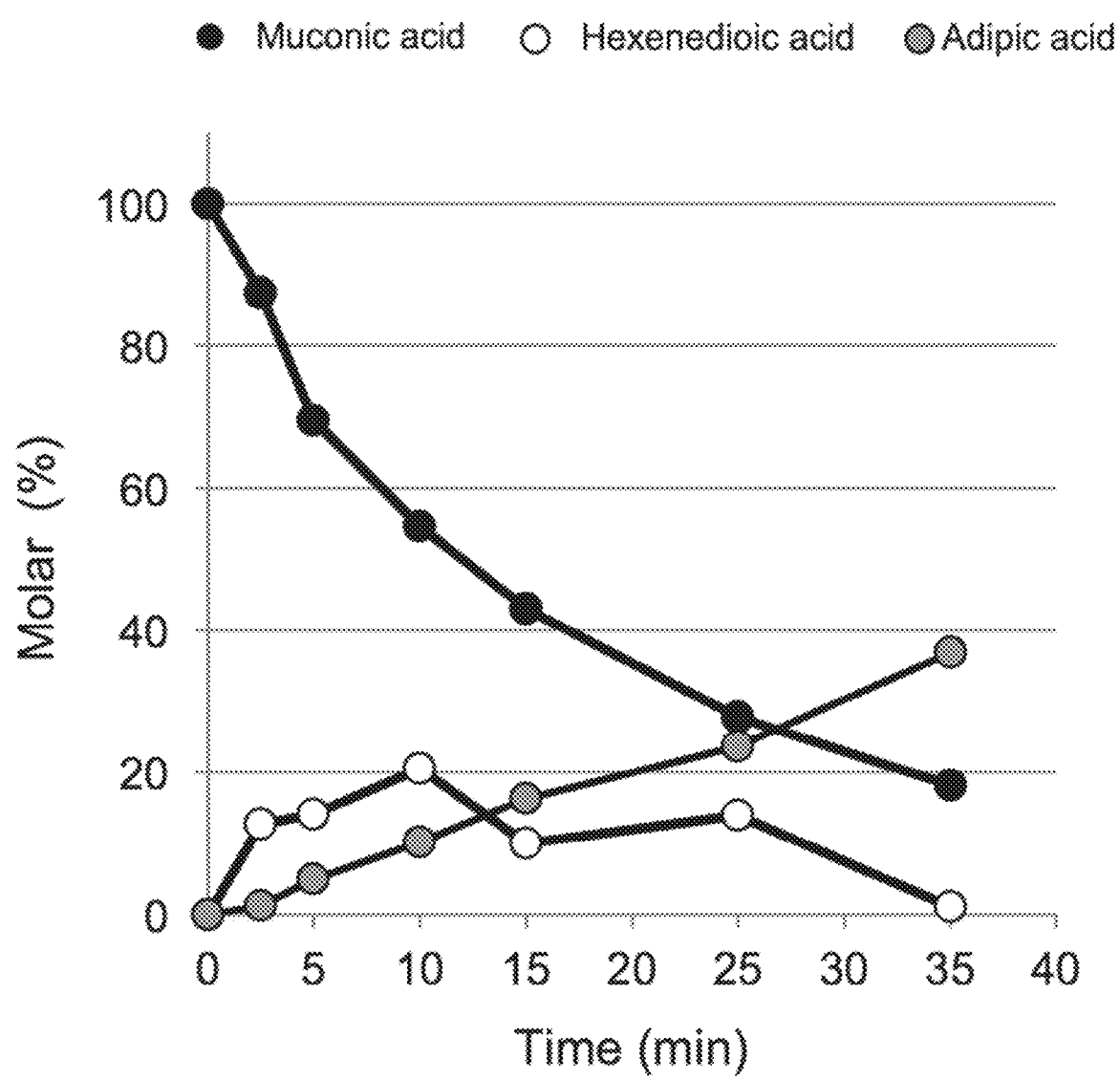

Both palladium catalysts were then exposed overnight to a saturated solution of muconic acid to induce fouling of the catalysts by organic adsorption, with subsequent testing of the fouled catalysts' activities for muconic acid hydrogenation. When normalized to an exposed surface metal site basis, fresh palladium catalysts displayed a muconic acid hydrogenation turn over frequency (TOF) ranging from 20-40 sec$^{-1}$, regardless of the support. With regards to hydrogenation productivity (normalized to the mass of muconic acid converted per mass of catalyst), the fresh 1% Pd/AC Alfa Aesar catalyst displayed a muconic acid hydrogenation productivity of 0.051 sec$^{-1}$. In contrast, the fouled commercial 1% Pd/AC catalyst showed a dramatic reduction in hydrogenation productivity to 0.017 sec$^{-1}$, which is a drop of over 60% from the fresh catalyst performance (see Table 5 and FIG. 7). In addition, leaching was also significant with 0.8% of the loaded original catalyst palladium dissolving into solution. In comparison, the fouled 1% Pd/$TiO_2$ Saint-Gobain catalyst having the 5-cycle $Al_2O_3$ ALD coating showed no significant drop in performance, with a hydrogenation productivity of 0.161 sec$^{-1}$. Furthermore, leaching of palladium was below in the 5-cycle $Al_2O_3$ ALD coated 1% Pd/$TiO_2$ Saint-Gobain catalyst, highlighting the benefit of using catalysts with ALD coatings and low surface area solid oxide supports for stabilizing muconic acid hydrogenation.

High fresh catalyst productivity was also observed with the 5-cycle $TiO_2$ ALD coated 1% Pd/$TiO_2$ Saint-Gobain catalyst (see Table 5), although follow-on stability testing was not performed.

coatings that maintain the surface morphology of the underlying material, with the inherent ability to enable mass transport through porosity due to nanometer sized cracking, reduced density, and/or incomplete coverage. Such coatings may encapsulate or partially encapsulate system components including but not limited to: dispersed particles down to the nanometer size range supported on the substrate, catalyst support materials, membranes, mesoporous materials, and other active layers. A coating may serve as a passive barrier to catalyst components and material diffusion, environmental barriers, membranes, and active catalytic components. Material types that may serve as coating include oxides, nitrides, sulfides, and/or pure elements. Examples of specific materials include but are not limited to: aluminum oxide, zinc oxide, titanium oxide, iron oxide, zinc sulfide, tin oxide, platinum, palladium, ruthenium, and nickel. Other functional components of the composites include particles (sized down to the nanometer length scale), layers, partial layers, and pores formed by lost wax method may be fabricated with sequential vapor-phase deposition. In some embodiments of the present disclosure, alternating deposition of coatings and particles, e.g. nanoparticles, directly formed by the deposition may produce concentric layers of particles encapsulated in the coating. Porosity in the coating described would enable mass transport to the dispersed nanoparticles. An example would be layers of aluminum oxide alternated with layers of discrete platinum nanoparticles. FIG. 3 illustrates a schematic of a possible catalyst architecture obtained from sequential deposition including multi-metal particle layers and hierarchical coatings that serve additional catalytic purposes. The primary vapor-phase synthesis method is thermal ALD, which relies on the self-limiting reactions determined by a temperature process window that enable layer-by-layer deposition.

In some embodiments of the present disclosure, vapor phase self-liming reactions at a material surface may be used to create and/or control active chemical sites through constructive and/or destructive processes. Principle strategies using ALD and/or atomic layer etching (ALE) may be utilized to achieve the desired results. ALD and ALE may use metal ligand exchange processes to deposit and or etch out specific chemical sites. These concepts may be applied to control active chemical sites. Some of these include but are not limited to Lewis acid/base sites, Brønsted acid/base sites, catalyst nanoparticles, etc. In some embodiments of the present disclosure, ALE may be used to remove aluminum atoms from a preformed substrate or ALD material to create a vacancy. The vacancy may remain for catalytic

TABLE 5

| Catalyst Material Description | Batch Fresh TOF (sec$^{-1}$) | Batch Fresh Productivity (sec$^{-1}$) | Batch Fouled Productivity (sec$^{-1}$) | Batch Pd Leaching in Solution (%) |
| --- | --- | --- | --- | --- |
| Uncoated 1% Pd/AC Alfa Aesar | 20-40 | 0.051 | 0.017 | 0.8% of initial Pd metal |
| 5-cycle ALD $Al_2O_3$ 1% Pd/$TiO_2$ Saint-Gobain | 20-40 | >0.200 | 0.161 | Below detection limit |
| 5-cycle ALD $TiO_2$ 1% Pd/$TiO_2$ Saint-Gobain | Not measured | 0.110 | Not measured | Not measured |

In some embodiments of the present disclosure, a coating may be constructed with conformal coatings, defined as functionality or be filled via ALD with a different atom. Another embodiment would be to first use ALD to fabricate a material whereupon a single-layer deposition of the one material is performed, followed by subsequent ALD of a second, differing material. The second material may act as an embedded site for catalytic function.

Tailoring ALD Cycle Number for Activity and Stability: The 1% Pd/Al$_2$O$_3$ Sigma Aldrich catalyst was initially coated with a series of ALD cycles (1, 5, 10 cycles) using TMA and H$_2$O precursors to determine the influence of ALD cycle number on powder catalyst activity and leaching stability. The suite of ALD-coated catalysts was then characterized and tested, as shown in Table 6 and FIGS. 8A-8D. ICP-MS analysis confirmed that the catalyst Al content increased with ALD cycle number, from 5.3 to 24.2 wt % of additional Al, with weight percent based on the mass of the final catalyst including any ALD coating. Likewise, the Pd content decreased with increasing ALD cycle number, with Pd content defined as wt % of the total catalyst including the ALD coating. Physisorption analysis showed a range of surface areas that varied from 92 to 102 m$^2$ g$^{-1}$ for the uncoated and 1- to 5-cycle catalysts (uncoated 99 m$^2$ g$^{-1}$; 1-cycle 102 m$^2$ g$^{-1}$; 5-cycle 92 m$^2$ g$^{-1}$). However, the 10-cycle ALD catalyst showed a dramatic decrease in surface area to 66 m$^2$ g$^{-1}$. With regards to Pd active site accessibility, the 1-cycle and 5-cycle ALD catalysts retained 94% and 90% surface Pd accessibility compared to the uncoated catalyst, respectively, as indicated by CO chemisorption (uncoated 29.8 micromol g$^{-1}$; 1-cycle 27.9 micromol g$^{-1}$; 5-cycle 26.7 micromol g$^{-1}$). However, the 10-cycle ALD catalyst retained only 6% Pd accessibility (10-cycle 1.9 μmol g$^{-1}$). Both the CO chemisorption and physisorption results indicate a nonlinear decrease in support surface area and Pd accessibility with increasing ALD cycle number in the range of 1 to 10 cycles for the 1% Pd/Al$_2$O$_3$ Sigma Aldrich catalyst.

Based on the promising hydrogenation productivity and stability results for the 5-cycle ALD catalyst, continuous testing was performed in a trickle-bed flow reactor. After 24 hours of time on stream, the 5-cycle catalyst retained 69% of the continuous hydrogenation productivity (mass of muconic acid converted per hour per mass of catalyst), compared to the uncoated catalyst (uncoated 6.50 h$^{-1}$; 5-cycle 4.50 h$^{-1}$). Furthermore, the 5-cycle catalyst reduced Pd leaching by 2.3-fold (uncoated 1.95 ppm; 5-cycle 0.84 ppm).

Broad Applicability of Low Cycle ALD: To further evaluate the applicability of low cycle ALD, a suite of Pd catalysts were prepared with Al$_2$O$_3$ or TiO$_2$ ALD coating. The suite of uncoated Pd catalysts included the following: (a) 0.7% Pd/TiO$_2$ Alfa Aesar, (b) 1% Pd/Al$_2$O$_3$ Sigma Aldrich, and (c) eggshell 0.5% Pd/Al$_2$O$_3$ pellets Alfa Aesar.

The 0.7% Pd/TiO$_2$ Alfa Aesar granular catalyst was coated with 5 cycles of Al$_2$O$_3$ ALD. As shown in Table 7 and FIGS. 9A and 9B, ALD coating the Pd/TiO$_2$ catalyst resulted in an Al content of 2.5 wt % that decreased the surface area by 22% (uncoated 146 m$^2$ g$^{-1}$; 5-cycle 114 m$^2$ g$^{-1}$). The comparatively high decrease in surface area with the TiO$_2$ support compared to the Al$_2$O$_3$ support is likely associated with differences in the physical and chemical properties of the substrates (e.g., porosity, hydroxyl density, reducibility). The 5-cycle Al$_2$O$_3$ ALD coated Pd/TiO$_2$ catalyst retained 51% of the surface Pd accessibility compared to the uncoated catalyst, as determined by CO chemisorption (uncoated 34.7 micromol g$^{-1}$; 5-cycle 17.6 micromol g$^{-1}$). Batch reactor testing determined that 31% of the catalyst hydrogenation productivity was retained, (uncoated 0.094

TABLE 6

| Catalyst Material Description | ICP-MS Loading (wt %) | Surface Area (m$^2$ g$^{-1}$) | CO Uptake (μmol g$^{-1}$) | Batch TOF (sec$^{-1}$) | Batch Productivity (sec$^{-1}$) | Batch Pd Leaching (ppm) | Flow Productivity (h$^{-1}$) | Flow Pd Leaching (ppm) |
|---|---|---|---|---|---|---|---|---|
| Uncoated 1% Pd/Al$_2$O$_3$ Sigma Aldrich | Pd 1.00 | 99 | 29.8 | 39 | 0.164 | 2.8 | 6.50 | 1.95 |
| 1-cycle Al$_2$O$_3$ 1% Pd/Al$_2$O$_3$ Sigma Aldrich | Pd 0.80 Al 5.3 | 102 | 27.9 | 24 | 0.095 | 2.4 | Not measured | Not measured |
| 5-cycle Al$_2$O$_3$ 1% Pd/Al$_2$O$_3$ Sigma Aldrich | Pd 0.70 Al 6.7 | 92 | 26.7 | 29 | 0.110 | 1.3 | 4.50 | 0.84 |
| 10-cycle Al$_2$O$_3$ 1% Pd/Al$_2$O$_3$ Sigma Aldrich | Pd 0.55 Al 24.2 | 66 | 1.90 | 42 | 0.011 | <0.01 | Not measured | Not measured |

Figure 9A:
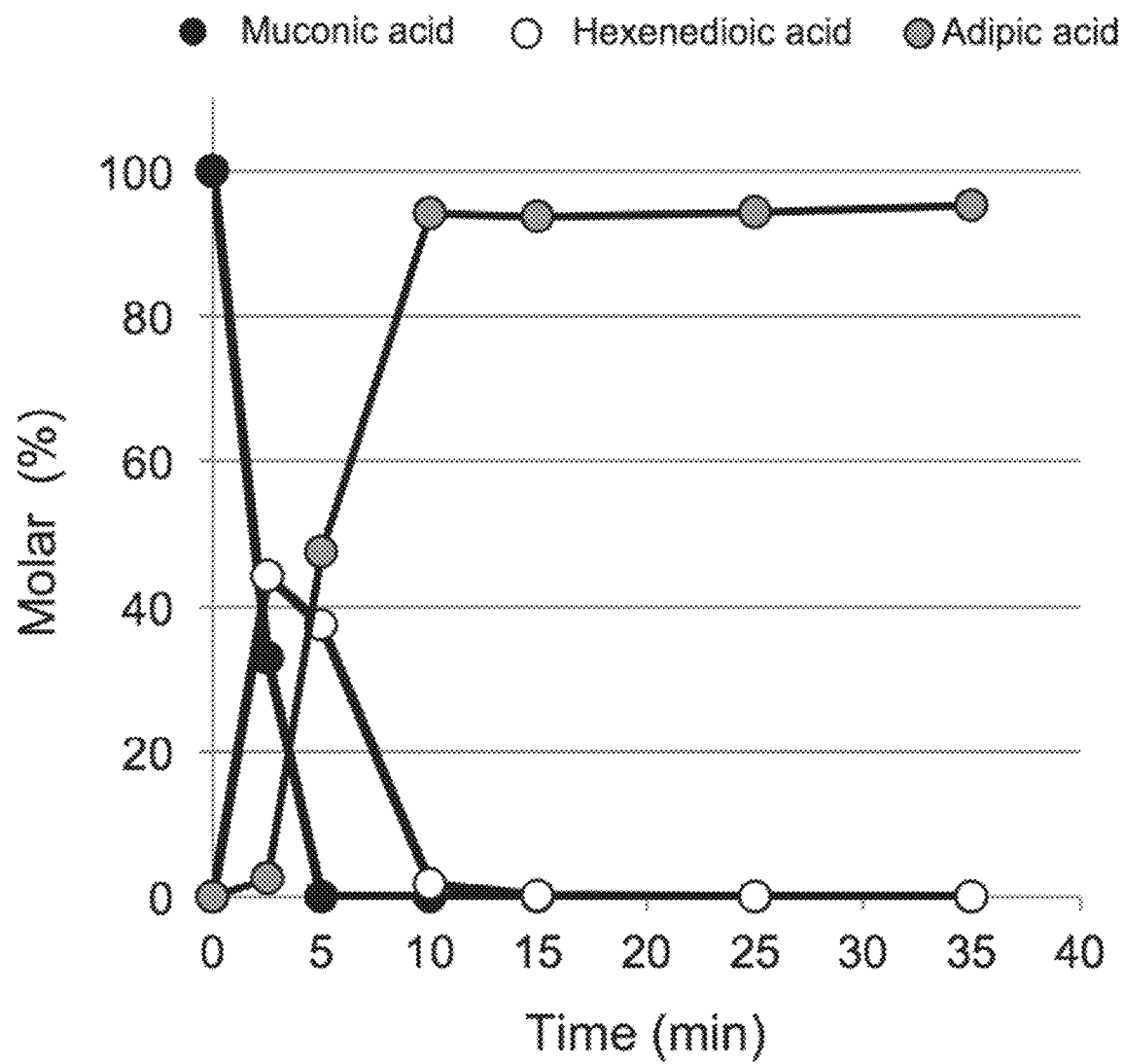
FIGS. 9A and 9B illustrate catalyst activity and selectivity of the uncoated (FIG. 9A) and 5-cycle $Al_2O_3$ ALD coated 1% $Pd/TiO_2$ catalyst prepared in house using an Alfa Aesar $TiO_2$ support (FIG. 9B), according to some embodiments of the present disclosure. Reaction conditions were as follows: 20 mL 1 wt % muconic acid in ethanol, 24° C., 24 bar $H_2$, 15 mg catalyst, stirring 1600 rpm.
Figure 9B:
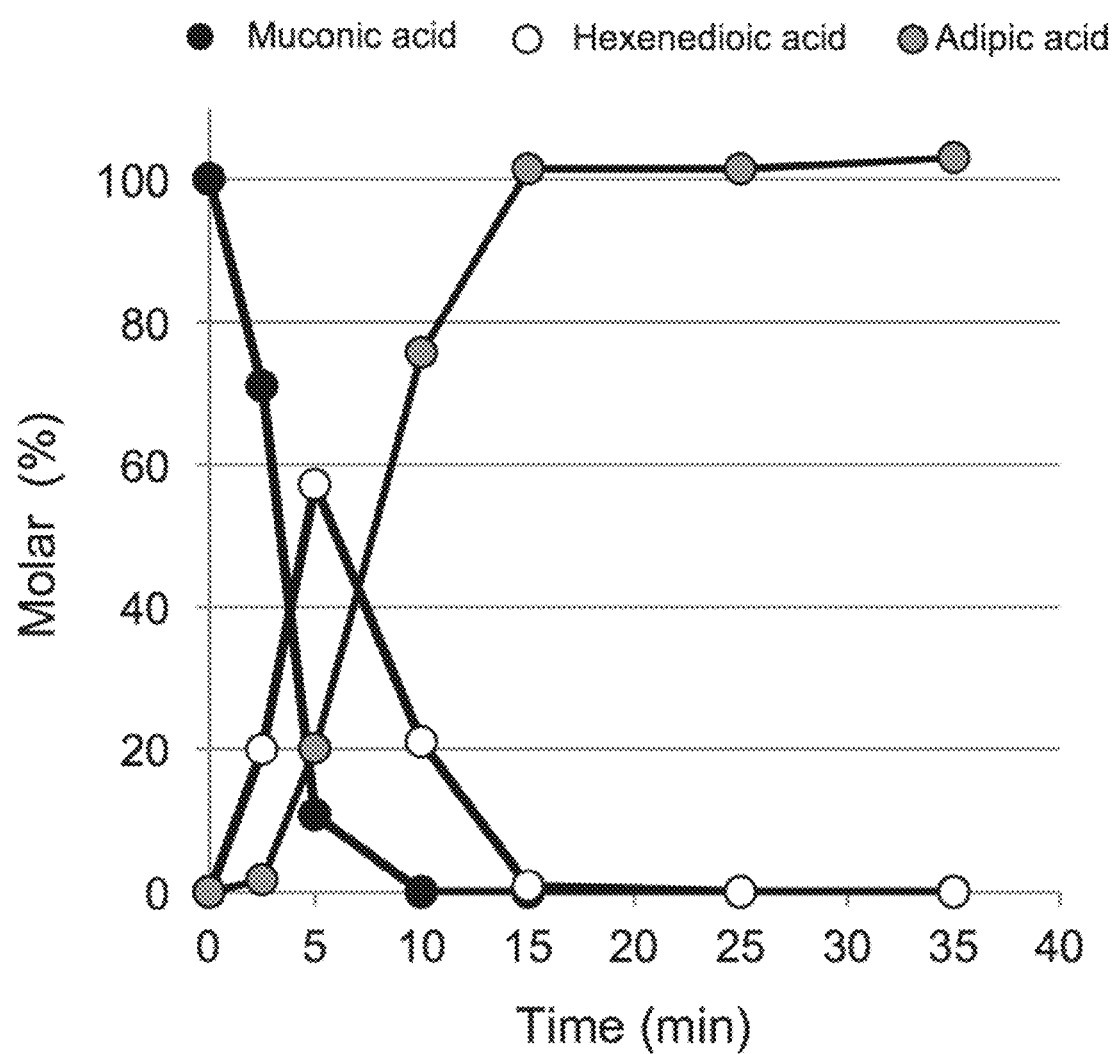
Figure 10:
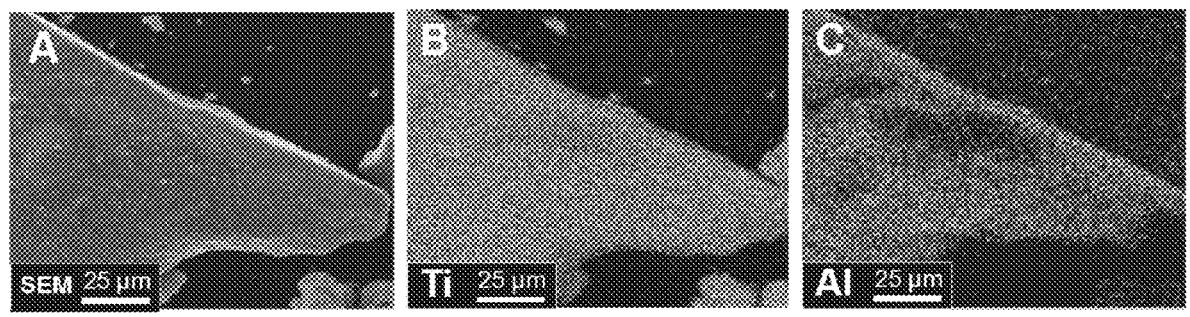
FIG. 10 illustrates SEM-EDX imaging (Panel A) and elemental mapping (Panels B and C) of the 5-cycle $Al_2O_3$ ALD coated 1% $Pd/TiO_2$ Alfa Aesar catalyst.

The trend in Pd accessibility was further supported by batch reactor hydrogenation productivity tests with muconic acid. The 1-cycle and 5-cycle ALD catalysts retained 58% and 68% of the batch reactor productivity, respectively, compared to the uncoated catalyst (uncoated 0.164 sec$^{-1}$; 1-cycle 0.095 sec$^{-1}$; 5-cycle 0.110 sec$^{-1}$), with no loss in adipic acid selectivity (see FIGS. 8A-8D). In contrast, the 10-cycle ALD catalyst retained only 7% of the uncoated catalyst activity (10-cycle 0.011 sec$^{-1}$). The Pd site TOF (mole of muconic acid converted per sec per mole of catalyst surface Pd) fell within a range of 24 to 42 sec$^{-1}$ for all catalysts. With regards to catalyst stability, batch reactor Pd leaching analysis determined that the 1-cycle and 5-cycle ALD catalysts reduced Pd leaching by 1.2-fold and 2.2-fold, respectively, compared to the uncoated catalyst (uncoated 2.8 ppm; 1-cycle 2.4 ppm; 5-cycle 1.3 ppm).

sec$^{-1}$; 5-cycle 0.029 sec$^{-1}$), with no major change in adipic acid selectivity (FIGS. 9A and 9B). The intrinsic Pd activity, determined by TOF measurements, fell within the range of 12 to 19 sec$^{-1}$. ICP-MS analysis of the reactor filtrate confirmed a 3.2-fold reduction in Pd leaching with the 5-cycle Al$_2$O$_3$ ALD coated catalyst (uncoated 8.1 ppm; 5-cycle 2.5 ppm). Due to the differing elemental composition of the ALD coating and catalyst support, SEM-EDS was able to confirm uniformly distributed Ti on the catalyst surface after ALD coating (FIG. 10). Lastly, flow reactor testing determined that after 24 hours of time on stream, the 5-cycle Al$_2$O$_3$ ALD coated catalyst retained 75% of the continuous hydrogenation productivity (uncoated 0.81 h$^{-1}$; 5-cycle 0.61 h$^{-1}$), with a 3.5-fold reduction in Pd leaching (uncoated 2.25 ppm; 5-cycle 0.65 ppm).

TABLE 7

| Catalyst Material Description | ICP-MS Loading (wt %) | Surface Area ($m^2\ g^{-1}$) | CO Uptake ($\mu mol\ g^{-1}$) | Batch TOF ($sec^{-1}$) | Batch Productivity ($sec^{-1}$) | Batch Pd Leaching (ppm) | Flow Productivity ($h^{-1}$) | Flow Pd Leaching (ppm) |
|---|---|---|---|---|---|---|---|---|
| Uncoated 0.7% Pd/TiO$_2$ Alfa Aesar | Pd 0.70 | 146 | 34.7 | 19 | 0.094 | 8.1 | 0.81 | 2.25 |
| 5 cycle Al$_2$O$_3$ 0.7% Pd/TiO$_2$ Alfa Aesar | Pd 0.66 Al 2.5 | 114 | 17.6 | 12 | 0.029 | 2.5 | 0.61 | 0.65 |

Figure 11A:
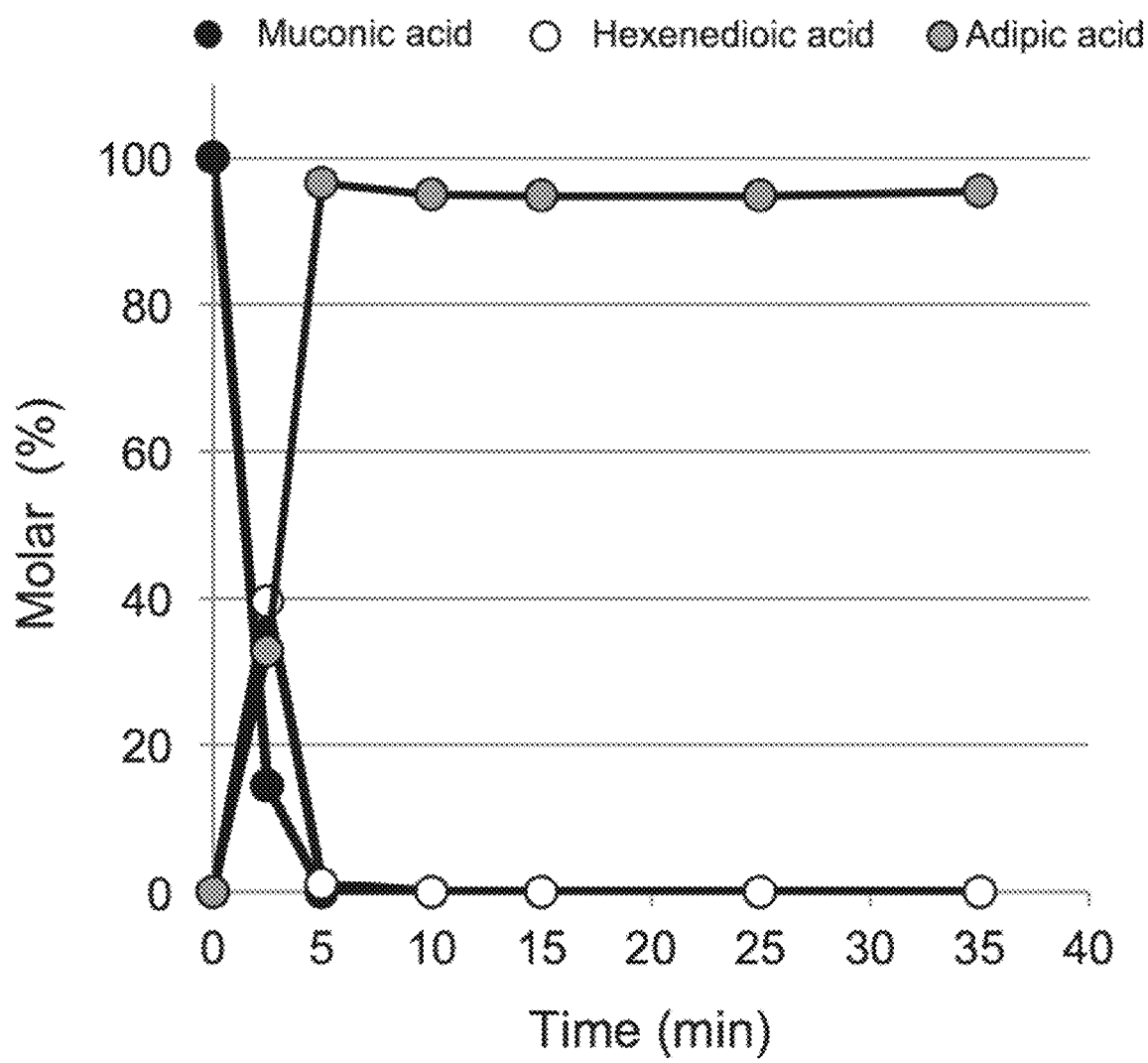
FIGS. 11A and 11B illustrate catalyst activity and selectivity for the uncoated (FIG. 11A) and 5-cycle $TiO_2$ ALD overcoated 1% $Pd/Al_2O_3$ Sigma Aldrich catalyst (FIG. 11B), according to some embodiments of the present disclosure. Reaction conditions were as follows: 20 mL 1 wt % muconic acid in ethanol, 24° C., 24 bar $H_2$, 15 mg catalyst, stirring 1600 rpm.
Figure 11B:
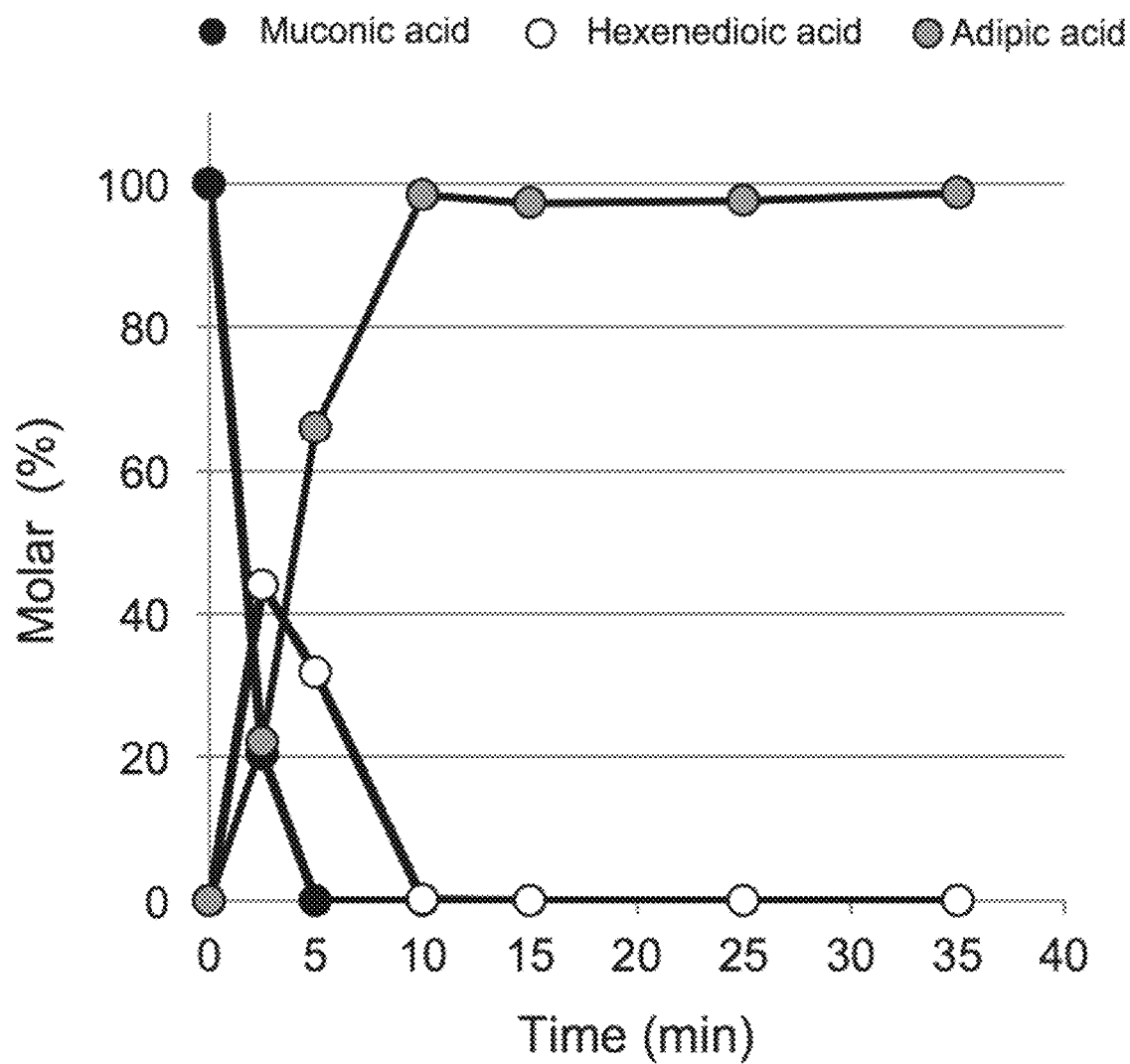

The 1% Pd/Al$_2$O$_3$ Sigma Aldrich powder catalyst was coated with 5 cycles of TiO$_2$ ALD. As shown in Table 8 and FIGS. 11A and 11B, the TiO$_2$ ALD coated 1% Pd/Al$_2$O$_3$ catalyst resulted in a Ti content of 4.0 wt %, with negligible change in surface area (uncoated 99 m$^2$ g$^{-1}$; 5-cycle 102 m$^2$ g$^{-1}$). The 5-cycle TiO$_2$ ALD coated catalyst retained 94% of Pd active site accessibility by CO chemisorption (uncoated 29.8 micromol g$^{-1}$; 5-cycle 27.9 micromol$^{-1}$). Batch reactor testing determined that 78% of the catalyst hydrogenation productivity was retained, (uncoated 0.164 sec$^{-1}$; 5-cycle 0.128 sec$^{-1}$), with no major change in adipic acid selectivity (FIGS. 11A and 11B). The intrinsic Pd activity, determined by TOF measurements, fell within the range of 24 to 39 sec$^{-1}$. ICP-MS analysis of the batch reactor filtrate confirmed a 2.2-fold reduction in Pd leaching with the 5-cycle TiO$_2$ ALD coated catalyst (uncoated 2.8 ppm; 5-cycle 1.3 ppm).

TABLE 8

| Catalyst Description | ICP-MS Loading (wt %) | Surface Area ($m^2\ g^{-1}$) | CO Uptake ($\mu mol\ g^{-1}$) | Batch Rx TOF ($sec^{-1}$) | Batch Productivity ($sec^{-1}$) | Batch Pd Leaching (ppm) |
|---|---|---|---|---|---|---|
| Uncoated 1% Pd/Al$_2$O$_3$ Sigma Aldrich | Pd 1.00 | 99 | 29.8 | 39 | 0.164 | 2.8 |
| 5-cycle TiO$_2$ 1% Pd/Al$_2$O$_3$ Sigma Aldrich | Pd 0.93 Ti 3.1 | 108 | 18.3 | 49 | 0.128 | 1.3 |

Figure 12A:
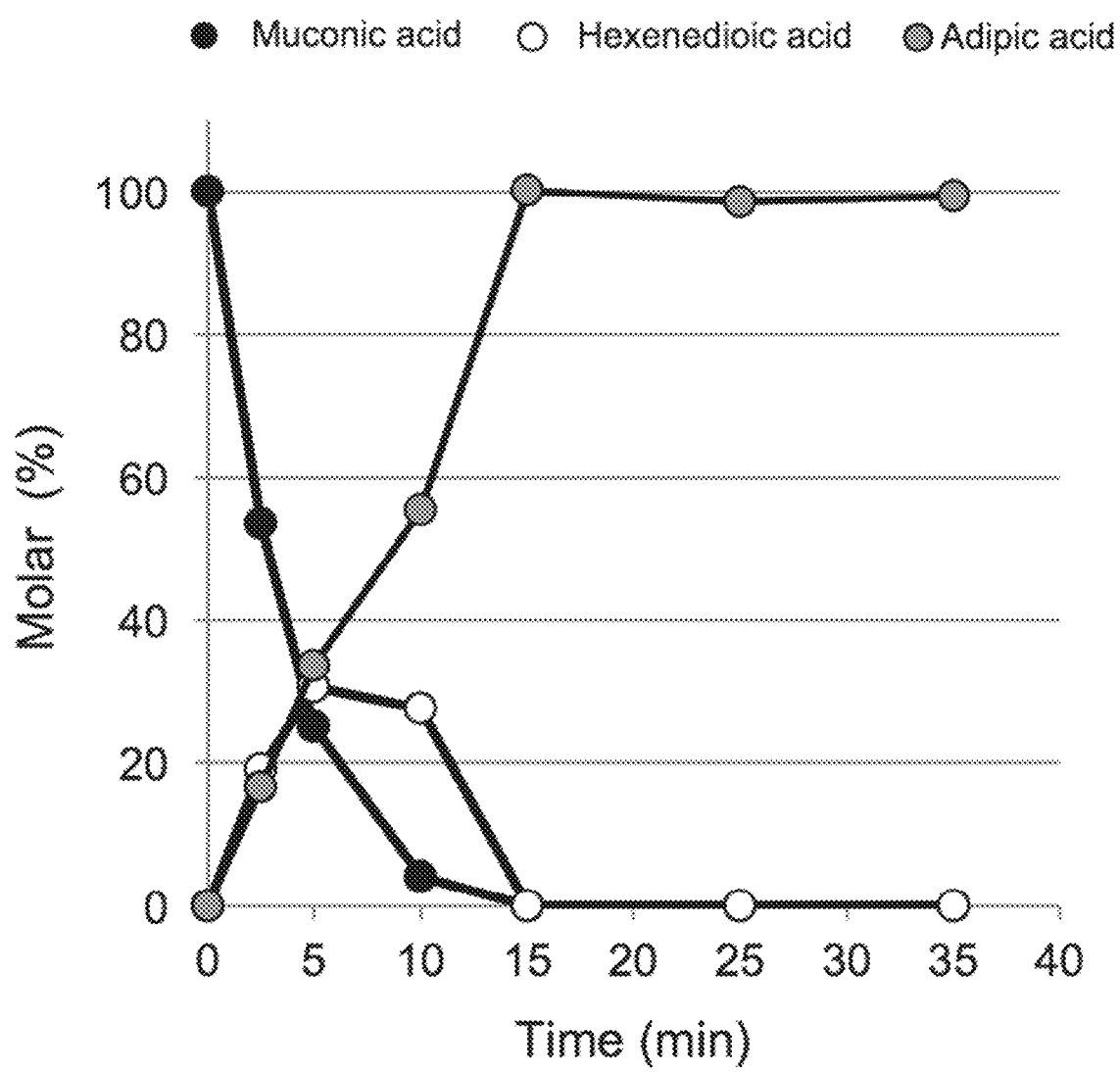
FIGS. 12A, 12B, and 12C illustrate catalyst activity and selectivity of the uncoated (FIG. 12A), 1-cycle (FIG. 12B), and 15-cycle $Al_2O_3$ ALD coated 0.5% $Pd/Al_2O_3$ eggshell Alfa Aesar catalyst (FIG. 12C), according to some embodiments of the present disclosure. Reaction conditions were as follows: 20 mL 1 wt % muconic acid in ethanol, 24° C., 24 bar $H_2$, 15 mg catalyst, stirring 1600 rpm.
Figure 12B:
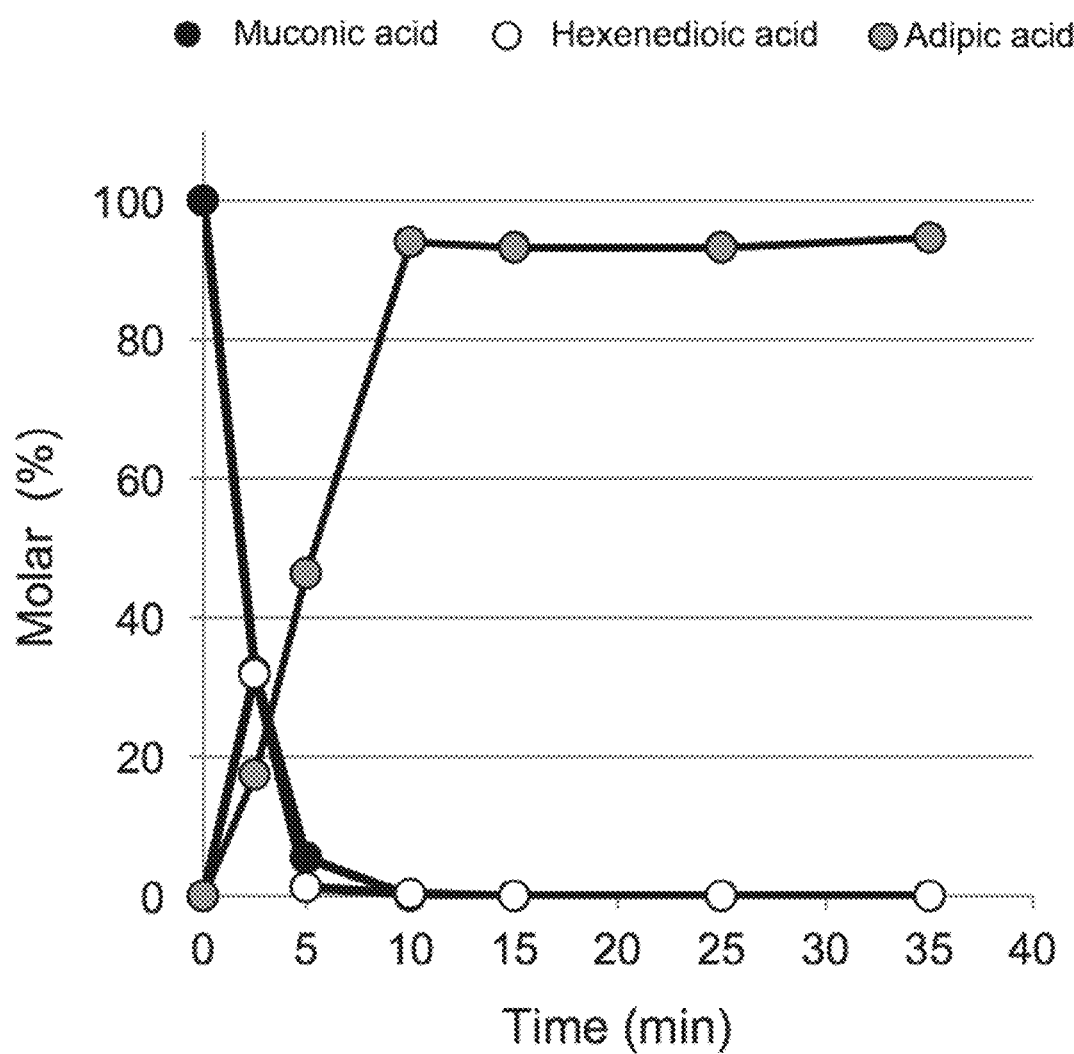
Figure 12C:
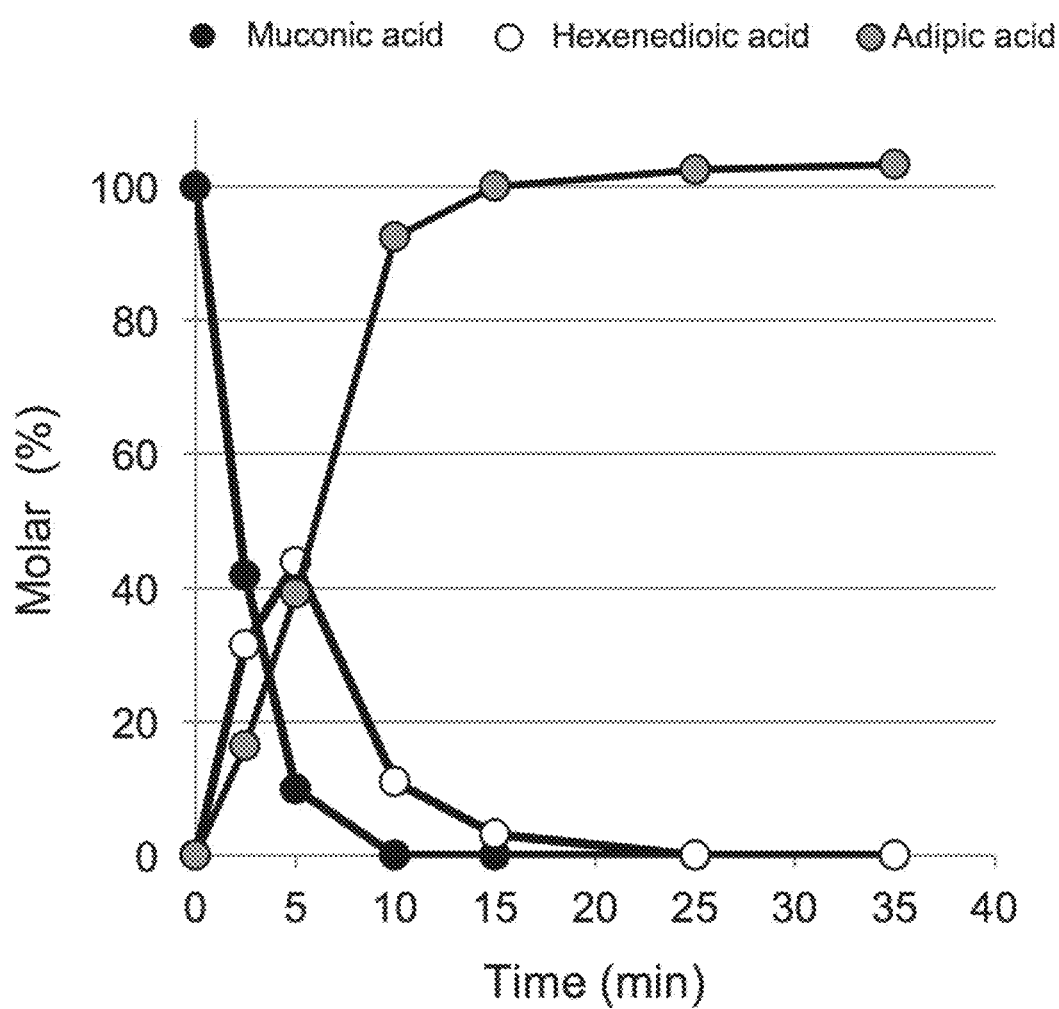

The 0.5% Pd/Al$_2$O$_3$ pellet catalyst was coated with 1 and 15 cycles of Al$_2$O$_3$ ALD. As shown in Table 9 and FIGS. 12A-12C, the Al$_2$O$_3$ ALD coated 0.5% Pd/Al$_2$O$_3$ pellet catalyst resulted in an additional Al content of 1.3 wt % and 9.66 wt % after 1 and 15 ALD cycles, respectively, with a decline in surface area with increasing ALD cycle number (uncoated 110 m$^2$ g$^{-1}$; 1-cycle 107 m$^2$ g$^{-1}$; 15-cycle 93 m$^2$ g$^{-1}$). Batch reactor testing observed no loss in catalyst hydrogenation productivity. The higher activity observed with the Al$_2$O$_3$ ALD coated catalysts compared to the uncoated 0.5% Pd/Al$_2$O$_3$ pellet catalyst may be due to variability in the uncoated catalyst Pd content loaded into the reactor after grinding sieving the eggshell catalyst material. No major change in adipic acid selectivity was observed with the Al$_2$O$_3$ ALD coated catalysts (FIGS. 11A and 11B). ICP-MS analysis of the batch reactor filtrate determined that 15 ALD cycles were necessary for a 2-fold reduction in Pd leaching with the pellet eggshell catalyst (uncoated 1.2 ppm; 1-cycle 0.8 ppm; 15-cycle 0.6 ppm). The higher cycle number required for leaching reduction may be due to the larger physical dimensions of the pellet that influence the ALD coating process, or differences in the chemical properties of the substrates (e.g., Pd site density, porosity, hydroxyl density, reducibility).

TABLE 9

| Catalyst Description | ICP-MS Loading (wt %) | Surface Area ($m^2\ g^{-1}$) | Batch Productivity ($sec^{-1}$) | Batch Pd Leaching (ppm) |
|---|---|---|---|---|
| Uncoated eggshell 0.5% Pd/Al$_2$O$_3$ | Pd 0.58 | 110 | 0.013 | 1.2 |
| 1-cycle Al$_2$O$_3$ eggshell 0.5% Pd/Al$_2$O$_3$ | Pd 0.47 Al 1.3 | 107 | 0.025 | 0.8 |
| 15-cycle Al$_2$O$_3$ eggshell 0.5% Pd/Al$_2$O$_3$ | Pd 0.47 Al 9.66 | 93 | 0.018 | 0.6 |

EXAMPLES

Example 1

A composition comprising: a solid support; a metal positioned on the solid support; and an oxide coating positioned to at least partially cover the metal.

Example 2

The composition of Example 1, wherein the solid support comprises at least one of a carbonaceous material or an oxide.

Example 3

The composition of either Example 1 or 2, wherein the oxide comprises at least one of silica, titanium oxide, or alumina.

Example 4

The composition of any one of Examples 1-3, wherein the carbonaceous material comprises an activated carbon.

Example 5

The composition of any one of Examples 1-4, wherein the solid support has a shape comprising at least one of spherical, cylindrical, or granular.

Example 6

The composition of any one of Examples 1-5, wherein the solid support has a first characteristic length between 1 micron and 10 mm.

Example 7

The composition of any one of Examples 1-6, wherein the first characteristic length is between 50 microns and 5 mm.

Example 8

The composition of any one of Examples 1-7, wherein the metal comprises a noble metal.

Example 9

The composition of any one of Examples 1-8, wherein the noble metal comprises at least one of ruthenium, rhodium, palladium, silver, osmium, iridium, platinum, or gold.

Example 10

The composition of any one of Examples 1-9, wherein the noble metal comprises palladium.

Example 11

The composition of any one of Examples 1-10, wherein the metal comprises a transition metal.

Example 12

The composition of any one of Examples 1-11, wherein the metal is present at a concentration between 0.1 wt % and 5.0 wt % relative to the metal and the solid support.

Example 13

The composition of any one of Examples 1-12, wherein the concentration is between 0.5 wt % and 1.0 wt %.

Example 14

The composition of any one of Examples 1-13, wherein the metal is in the form of a particle.

Example 15

The composition of any one of Examples 1-14, wherein the particle is in the shape of at least one of spherical, cylindrical, or granular.

Example 16

The composition of any one of Examples 1-15, wherein the particle has a second characteristic length of less than one micron.

Example 17

The composition of any one of Examples 1-16, wherein the second characteristic length is between 1 nanometer and 100 nanometers.

Example 18

The composition of any one of Examples 1-17, wherein the particle is at least one of crystalline, polycrystalline, or amorphous.

Example 19

The composition of any one of Examples 1-18, wherein the oxide coating covers substantially all of the metal.

Example 20

The composition of any one of Examples 1-19, wherein the oxide coating covers substantially all of the solid support.

Example 21

The composition of any one of Examples 1-20, wherein the oxide coating comprises at least one of silica, alumina, titanium oxide, cerium oxide, magnesium oxide, tin oxide, or nickel oxide.

Example 22

The composition of any one of Examples 1-21, wherein the oxide coating comprises at least one of silica, alumina, or titanium oxide.

Example 23

The composition of any one of Examples 1-22, wherein the oxide coating has a thickness between 0.1 nm and 100 nm.

Example 24

The composition of any one of Examples 1-23, wherein the thickness is between 1 nm and 5 nm.

Example 25

The composition of any one of Examples 1-24, wherein the oxide coating comprises at least one of a crack or a pore.

Example 26

The composition of any one of Examples 1-25, wherein the oxide coating comprises at least two oxide coatings.

Example 27

The composition of any one of Examples 1-26, wherein the oxide coating comprises between two oxide coatings and ten oxide coatings.

Example 28

The composition of any one of Examples 1-27, wherein the oxide coating comprises between two oxide coatings and five oxide coatings.

Example 29

The composition of any one of Examples 1-28, wherein each oxide coating has a thickness between 1 nm and 5 nm.

Example 30

The composition of any one of Examples 1-29, wherein the oxide coating provides an accessibility to the metal between 80% and 100% as measured by carbon monoxide chemisorption.

Example 31

The composition of any one of Examples 1-30, wherein the accessibility is between 85% and 95%.

Example 32

The composition of any one of Examples 1-31, further comprising: a second metal positioned on the oxide coating; and a second oxide coating positioned to at least partially cover the second metal.

Example 33

The composition of any one of Examples 1-32, further comprising: a third metal positioned on the second oxide coating; and a third oxide coating positioned to at least partially cover the third metal.

Example 34

The composition of any one of Examples 1-33, wherein at least one of the second metal and the third metal comprise at least one of a noble metal or a transition metal.

Example 35

The composition of any one of Examples 1-34, wherein at least one of the second oxide coating or the third oxide coating comprise at least one of silica, alumina, titanium oxide, cerium oxide, magnesium oxide, tin oxide, or nickel oxide.

Example 36

The composition of any one of Examples 1-35, further comprising a surface area between 25 $m^2/g$ and 200 $m^2/g$ as measured by nitrogen physisorption.

Example 37

The composition of any one of Examples 1-36, wherein the surface area is between 65 $m^2/g$ and 110 $m^2/g$.

Example 38

The composition of any one of Examples 1, further comprising: a surface area between 25 $m^2/g$ and 200 $m^2/g$ as measured by nitrogen physisorption, wherein: the metal comprises palladium, the solid support comprises at least one of titanium dioxide or alumina, the oxide coating comprises between one oxide coating and five oxide coatings of at least one of titanium dioxide or alumina, each oxide coating has a thickness between 1 nm and 5 nm, the metal has an accessibility between 85% and 95% as measured by carbon monoxide chemisorption, the metal is present at a concentration between 0.1 wt % and 1 wt % relative to the metal and the solid support, and the solid support is in the form of a cylinder having a characteristic length between 0.5 mm and 5 mm.

Example 39

A method comprising: contacting muconic acid and hydrogen with a catalyst comprising: a solid support; a metal positioned on the solid support; and an oxide coating positioned to at least partially cover the metal, wherein: the contacting is performed with the muconic acid in a liquid phase comprising an alcohol, and the contacting converts at least a portion of the muconic acid to adipic acid.

Example 40

The method of Example 39, wherein the contacting is performed at a pressure of up to 24 bar.

Example 41

The method of either Example 39 or 40, wherein the alcohol comprises ethanol.

Example 42

The method of any one of Examples 39-41, wherein the hydrogen is supplied at a pressure between 1 atmosphere and 100 atmosphere.

Example 43

The method of any one of Examples 39-42, wherein the contacting is performed in stirred tank reactor.

Example 44

The method of any one of Examples 39-43, wherein the contacting is performed by mixing at least the liquid phase and the catalyst at a speed of up to 1600 rpm.

Example 45

The method of any one of Examples 39-44, wherein the contacting is performed at a temperature between 20° C. and 100° C.

Example 46

The method of any one of Examples 39-45, wherein the contacting is performed in a packed-bed reactor.

Example 47

The method of any one of Examples 39-46, wherein the contacting is performed at a pressure at an inlet to the packed-bed reactor of up to 500 psig.

Example 48

The method of any one of Examples 39-47, wherein the catalyst has a characteristic length between about 0.5 mm and 5 mm.

The foregoing discussion and examples have been presented for purposes of illustration and description. The foregoing is not intended to limit the aspects, embodiments, or configurations to the form or forms disclosed herein. In the foregoing Detailed Description, for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A composition comprising:
   a solid support;
   a metal positioned on the solid support; and
   an oxide coating positioned to at least partially cover the metal; and
   wherein:
      the metal comprises palladium,
      the solid support comprises at least one of titanium dioxide or alumina,
      the oxide coating comprises between one oxide coating and five oxide coatings of at least one of titanium dioxide or alumina,
      each oxide coating has a thickness between 1 nm and 5 nm,
   the metal has an accessibility between 85% and 95% as measured by carbon monoxide chemisorption,
   the metal is present at a concentration between 0.1 wt % and 1 wt % relative to the metal and the solid support, and
   the solid support is in the form of a cylinder having a characteristic length between 0.5 mm and 5 mm and a surface area between 25 m$^2$/g and 200 m$^2$/g as measured by nitrogen physisorption.

2. The composition of claim 1, wherein the solid support has a first characteristic length between 1 micron and 10 mm.

3. The composition of claim 1, wherein the metal comprises at least one of ruthenium, rhodium, palladium, silver, osmium, iridium, platinum, or gold.

4. The composition of claim 1, wherein the metal is present at a concentration between 0.1 wt % and 2.4% and at a concentration between 2.6% and 5.0 wt % relative to the metal and the solid support.

5. The composition of claim 1, wherein the metal is in the form of a particle having a second characteristic length of less than one micron.

6. The composition of claim 1, wherein the oxide coating comprises at least one of silica, titanium oxide, cerium oxide, magnesium oxide, tin oxide, or nickel oxide.

7. The composition of claim 1, wherein the oxide coating has a thickness between 0.4 nm and 100 nm.

8. The composition of claim 1, wherein the oxide coating comprises at least one of a crack or a pore.

9. A method comprising:
   contacting muconic acid and hydrogen with a catalyst comprising:
      a solid support;
      a metal positioned on the solid support; and
      an oxide coating positioned to at least partially cover the metal,
   wherein:
      the metal comprises palladium,
      the solid support comprises at least one of titanium dioxide or alumina,
      the oxide coating comprises between one oxide coating and five oxide coatings of at least one of titanium dioxide or alumina,
      each oxide coating has a thickness between 1 nm and 5 nm,
      the metal has an accessibility between 85% and 95% as measured by carbon monoxide chemisorption,
      the metal is present at a concentration between 0.1 wt % and 1 wt % relative to the metal and the solid support, and
      the solid support is in the form of a cylinder having a characteristic length between 0.5 mm and 5 mm and a surface area between 25 m$^2$/g and 200 m$^2$/g as measured by nitrogen physisorption,
   wherein:
      the contacting is performed with the muconic acid in a liquid phase comprising an alcohol, and
      the contacting converts at least a portion of the muconic acid to adipic acid.

10. The method of claim 9, wherein the alcohol comprises ethanol.

11. The method of claim 9, wherein the hydrogen is supplied at a pressure between 1 atmosphere and 100 atmosphere.

12. The method of claim 9, wherein the contacting is performed in a stirred tank reactor.

13. The method of claim 9, wherein the contacting is performed at a temperature between 20° C. and 100° C.

14. The method of claim 9, wherein the contacting is performed in a packed-bed reactor.

* * * * *